United States Patent
Matsuno et al.

(10) Patent No.: US 9,982,106 B2
(45) Date of Patent: *May 29, 2018

(54) POROUS RESIN PARTICLES, METHOD OF MANUFACTURING POROUS RESIN PARTICLES, DISPERSION LIQUID, AND USE OF POROUS RESIN PARTICLES

(71) Applicant: Sekisui Plastics Co., Ltd., Osaka-shi (JP)

(72) Inventors: Shinya Matsuno, Koka (JP); Masaaki Nakamura, Koka (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 21 days.

This patent is subject to a terminal disclaimer.

(21) Appl. No.: 14/781,093

(22) PCT Filed: Mar. 20, 2014

(86) PCT No.: PCT/JP2014/057860
§ 371 (c)(1),
(2) Date: Sep. 29, 2015

(87) PCT Pub. No.: WO2014/156994
PCT Pub. Date: Oct. 2, 2014

(65) Prior Publication Data
US 2016/0053067 A1    Feb. 25, 2016

(30) Foreign Application Priority Data

Mar. 29, 2013    (JP) .................. 2013-074210

(51) Int. Cl.
*C08J 9/14*    (2006.01)
*A61Q 1/12*    (2006.01)
(Continued)

(52) U.S. Cl.
CPC .............. *C08J 9/142* (2013.01); *A61K 8/0279* (2013.01); *A61K 8/8152* (2013.01); *A61Q 1/02* (2013.01);
(Continued)

(58) Field of Classification Search
CPC ................ A61K 8/8152; A61K 8/0279; A61K 2800/412; C08J 3/12
See application file for complete search history.

(56) References Cited

U.S. PATENT DOCUMENTS 5,608,005 A    3/1997    Sojka
5,618,877 A    4/1997    Tomlin et al.
(Continued)

FOREIGN PATENT DOCUMENTS

JP    60-184004 A    9/1985
JP    02-255704 A    10/1990
(Continued)

OTHER PUBLICATIONS

International Search Report dated Apr. 22, 2014, issued for PCT/JP2014/057860.

*Primary Examiner* — Jianfeng Song
(74) *Attorney, Agent, or Firm* — Wenderoth, Lind & Ponack, L.L.P.

(57) ABSTRACT

Disclosed are porous resin particles which contain a polymer of a monomer mixture of a mono(meth)acrylate-based monomer and a polyfunctional vinyl-based monomer. The mono(meth)acrylate-based monomer contains an ethylenic unsaturated group only in a (meth)acrylic acid residue, a hydroxyl group in an alcohol residue, and at least one of an ether group and an ester group in an alcohol residue. The polyfunctional vinyl-based monomer contains two or more ethylenic unsaturated groups. The porous resin particles have a water absorption value of from more than 400 ml to
(Continued)

700 ml per 100 g of the particles and an oil absorption value of from more than 400 ml to 700 ml per 100 g of the particles.

16 Claims, 4 Drawing Sheets

(51) Int. Cl.
    *A61K 8/81*     (2006.01)
    *C09D 135/02*     (2006.01)
    *A61K 8/02*     (2006.01)
    *A61Q 1/02*     (2006.01)
    *C08F 2/26*     (2006.01)
    *C08J 3/12*     (2006.01)

(52) U.S. Cl.
    CPC ................. *A61Q 1/12* (2013.01); *C08F 2/26* (2013.01); *C08J 3/12* (2013.01); *C09D 135/02* (2013.01); *A61K 2800/412* (2013.01); *C08J 2333/08* (2013.01); *C08J 2335/02* (2013.01)

(56) References Cited

U.S. PATENT DOCUMENTS

| | | | |
|---|---|---|---|
| 5,677,407 A | 10/1997 | Sojka | |
| 5,712,358 A | 1/1998 | Sojka | |
| 5,773,546 A | 6/1998 | Tomlin et al. | |
| 5,777,054 A | 7/1998 | Sojka | |
| 5,830,960 A | 11/1998 | Sojka | |
| 5,830,967 A | 11/1998 | Sojka | |
| 5,834,577 A | 11/1998 | Sojka | |
| 5,837,790 A | 11/1998 | Sojka | |
| 5,955,552 A | 9/1999 | Sojka | |
| 6,107,429 A | 8/2000 | Sojka | |
| 6,248,849 B1 | 6/2001 | Sojka | |
| 6,387,995 B1 | 5/2002 | Sojka | |
| 2011/0287076 A1* | 11/2011 | Harada | C08F 2/22 424/401 |
| 2012/0034281 A1* | 2/2012 | Kaneko | A61K 8/0241 424/401 |
| 2015/0004127 A1 | 1/2015 | Ishimori et al. | |

FOREIGN PATENT DOCUMENTS

| | | |
|---|---|---|
| JP | 4-51522 B2 | 8/1992 |
| JP | 06-254373 A | 9/1994 |
| JP | 2011-94124 A | 5/2011 |
| KR | 1998-079795 A | 11/1998 |
| WO | WO-2013/114653 A1 | 8/2013 |

\* cited by examiner

POROUS RESIN PARTICLES, METHOD OF MANUFACTURING POROUS RESIN PARTICLES, DISPERSION LIQUID, AND USE OF POROUS RESIN PARTICLES

TECHNICAL FIELD

The present invention relates in general to porous resin particles, a method of manufacturing the porous resin particles, a dispersion liquid, and use of the porous resin particles and in particular to porous resin particles with high water absorbance and high oil absorbance, a method of manufacturing the porous resin particles, a dispersion liquid containing the porous resin particles, and use of the porous resin particles (e.g., medicinal-ingredient-containing particles, external preparations, coating materials, light diffusion members, and liquid-chromatography separating agents containing the porous resin particles).

BACKGROUND ART

Conventional skin care products and other external preparations contain resin particles to fix skin flaws (to conceal spots, freckles, pores, etc.) by means of light scattering effects and to improve spreadability upon their application to the skin, as well as for various other purposes. Resin particles are also blended with coating materials and light diffusion members to exploit light scattering effects for matting or light diffusing purposes.

The external preparations containing resin particles are in some cases required to have improved sweat and sebum absorbance so that they can render the skin smooth and silky when applied to the skin. Therefore, the resin particles used with external preparations desirably have some water and oil absorbance.

For example, Patent Document 1 discloses a spherical polymer having an average particle diameter of 1 μm to 50 μm and an apparent specific gravity of 1.0 or less, each particle including one, two, or more spherical hollow tiny spaces inside it. The spherical polymer has some water and oil absorbance: 100 g of the spherical polymer is capable of absorbing 89.5 ml to 110 ml of water and 57.8 ml to 82.3 ml of oil (oleic acid).

Patent Document 2 discloses spherical porous fine cellulose particles with an outer shell layer and a porous inner core having a porosity of 5% to 50%. The spherical porous fine cellulose particles have some water and oil absorbance: 100 g of the particles are capable of absorbing 170 ml of water and 70 ml of oil.

Patent Document 3 discloses spherical porous resin powder having particle diameters of 1 μm to 40 μm and an average particle diameter of 2 μm to 20 μm, the powder including, on the spherical surface, pores of various sizes with mode pore diameters ranging from 5 angstroms to 160 angstroms (0.5 nm to 16 nm). The powder has some water and oil absorbance: 100 g of the powder is capable of absorbing 74.6 ml to 78.2 ml of water and 81.4 ml to 87.6 ml of oil (oleic acid).

Patent Document 4 discloses hollow flattened fine polymer particles with a shell wall made of an organic macromolecular compound. The hollow fine polymer particles become spherical upon absorbing a liquid substance and have some water and oil absorbance.

CITATION LIST

Patent Literature

Patent Document 1: Japanese Patent Application Publication, Tokukaisho, No. 60-184004

Patent Document 2: Japanese Patent Application Publication, Tokukaihei, No. 6-254373

Patent Document 3: Japanese Examined Patent Publication, Tokukouhei, No. 4-51522

Patent Document 4: Japanese Patent Application Publication, Tokukaihei, No. 2-255704

SUMMARY OF THE INVENTION

Problems to be Solved by the Invention

Although the particles disclosed in Patent Documents 1 to 3 have some water and oil absorbance, they are poor in either water absorbance or oil absorbance or in both. They do not exhibit both high water absorbance and high oil absorbance.

In contrast, the particles disclosed in Patent Document 4 appear to exhibit both high water absorbance and high oil absorbance because they have a shell wall made of an organic macromolecular compound that has a high degree of swelling (specifically, 1.5 to 10) in liquid substances (e.g., water and benzene). Each particle of Patent Document 4, however, has a single pore in it and is hollow. Therefore, the particles fall short of imparting sufficient light scattering effects to external preparations, coating materials, or light diffusion members when compared with porous-structure resin particles with a plurality of pores (porous resin particles). Although the particles of Patent Document 4 become spherical upon absorbing a liquid substance, they change shape, becoming flattened, after discharging the liquid substance. For this reason, for example, the coating film formed by applying and subsequently drying a coating material containing the particles disclosed in Patent Document 4 exhibits no light scattering, hence no matting effects, because the particles have already discharged the liquid substance and become flattened. Furthermore, the coating film gives poor sense of touch for the same reason. The particles of Patent Document 4 are hardly compatible with the binder resin blended with the particles to produce the coating material and easily come off the coating film.

The present invention, conceived in view of these conventional problems, has an object of providing porous resin particles with high water absorbance and high oil absorbance, a method of manufacturing the porous resin particles, a dispersion liquid containing the porous resin particles, and use of the porous resin particles.

Solution to Problem

To achieve the object, porous resin particles of the present invention contain a polymer of a monomer mixture which contains: a mono(meth)acrylate-based monomer containing: an ethylenic unsaturated group only in a (meth)acrylic acid residue; a hydroxyl group in an alcohol residue; and at least one of an ether group and an ester group in an alcohol residue; and a polyfunctional vinyl-based monomer containing two or more ethylenic unsaturated groups, the particles having a water absorption value of from more than 400 ml to 700 ml per 100 g of the particles and an oil absorption value of from more than 400 ml to 700 ml per 100 g of the particles.

The mono(meth)acrylate-based monomer contains a hydroxyl group, which is a hydrophilic group, and at least one of an ether group and an ester group, which are both a hydrophilic group, in an alcohol residue. The mono(meth) acrylate-based monomer therefore has high affinity for at least a dispersion medium selected from the group consisting of water and alcohols (hereinafter, referred to as a "hydrophilic dispersion medium"). The porous resin particles of the present invention contain a polymer of a monomer mixture containing the mono(meth)acrylate-based monomer and the polyfunctional vinyl-based monomer. The porous resin particles of the present invention therefore contain structural units derived from the acrylate-based monomer that has high affinity for the hydrophilic dispersion medium. The porous resin particles of the present invention hence have high affinity for the hydrophilic dispersion medium. In addition, the porous resin particles of the present invention exhibit a very high water absorption value of from more than 400 ml to 700 ml per 100 g of the particles and a very high oil absorption value of from more than 400 ml to 700 ml per 100 g of the particles, as well as high affinity for the hydrophilic dispersion medium. In addition, the porous resin particles of the present invention have a porous structure and therefore, when blended in external preparations, coating materials, or light diffusion members, impart strong light scattering effects to the external preparations, coating materials, and light diffusion members. Furthermore, the porous resin particles of the present invention have excellent redispersibility in the hydrophilic dispersion medium due to their high affinity for the hydrophilic dispersion medium.

Note that throughout the present specification, "(meth) acrylic" means acrylic or methacrylic, and "(meth)acrylate" means acrylate or methacrylate. In addition, throughout the present specification, the "water absorption value" refers to the amount of water absorbed as measured by the method that will be described later in detail in the examples of the invention, and the "oil absorption value" refers to the amount of oil absorbed as measured by the method that will be described later in detail in the examples of the invention. Again throughout the present specification, "light diffusion" encompasses diffusion of both reflected light and transmitted light.

A method of manufacturing porous resin particles of the present invention includes the step of suspension-polymerizing a monomer mixture in the presence of a non-polymerizable organic solvent as a pore-forming agent, the monomer mixture containing: a mono(meth)acrylate-based monomer in an amount of from 2 wt % to less than 30 wt % containing: an ethylenic unsaturated group only in a (meth) acrylic acid residue; a hydroxyl group in an alcohol residue; and at least one of an ether group and an ester group in an alcohol residue; and a polyfunctional vinyl-based monomer in an amount of from more than 70 wt % to 98 wt % containing two or more ethylenic unsaturated groups, the pore-forming agent being used in the step in an amount of from 200 parts by weight to 500 parts by weight per 100 parts by weight of the monomer mixture.

According to the manufacturing method of the present invention, in the step of suspension-polymerizing a monomer mixture in the presence of a non-polymerizable organic solvent as a pore-forming agent, a pore-forming agent is used in an amount of from 200 parts by weight to 500 parts by weight per 100 parts by weight of a monomer mixture that contains the mono(meth)acrylate-based monomer in an amount of from 2 wt % to less than 30 wt % and the polyfunctional vinyl-based monomer in an amount of from more than 70 wt % to 98 wt %. The method is therefore capable of manufacturing porous resin particles that exhibit high water absorbance and high oil absorbance and when blended in an external preparation, coating material, or light diffusion member, impart strong light scattering effects to the external preparation, coating material, and light diffusion member. Furthermore, the manufacturing method of the present invention uses a monomer mixture containing the mono(meth)acrylate-based monomer and the polyfunctional vinyl-based monomer in respective, predetermined relative amounts. The porous resin particles obtained by the method therefore contain structural units derived from the acrylate-based monomer that has high affinity for the hydrophilic dispersion medium. The porous resin particles hence have high affinity for the hydrophilic dispersion medium.

A dispersion liquid of the present invention contains: the porous resin particles of the present invention; and at least one dispersion medium selected from the group consisting of water and alcohols.

The dispersion liquid of the present invention exhibits high water absorbance and high oil absorbance because it contains the porous resin particles of the present invention which exhibit high water absorbance and high oil absorbance.

An external preparation of the present invention contains the porous resin particles of the present invention.

The external preparation of the present invention exhibits high water absorbance and high oil absorbance because it contains the porous resin particles of the present invention which exhibit high water absorbance and high oil absorbance.

Medicinal-ingredient-containing particles of the present invention contain the porous resin particles of the present invention and a medicinal ingredient.

The medicinal-ingredient-containing particles of the present invention are expected to provide a lasting pharmacological benefit when applied to the skin because it contains the porous resin particles of the present invention and a medicinal ingredient.

Another external preparation of the present invention contains the medicinal-ingredient-containing particles of the present invention.

This other external preparation of the present invention is expected to provide a lasting pharmacological benefit when applied to the skin because it contains the medicinal-ingredient-containing particles of the present invention.

A coating material of the present invention contains the porous resin particles of the present invention.

The coating material of the present invention exhibits high water absorbance and high oil absorbance because it contains the porous resin particles of the present invention which exhibit high water absorbance and high oil absorbance.

A light diffusion member of the present invention contains the porous resin particles of the present invention.

The light diffusion member of the present invention exhibits excellent light diffusibility because it contains the porous resin particles of the present invention.

A liquid-chromatography separating agent of the present invention contains the porous resin particles of the present invention.

The liquid-chromatography separating agent of the present invention is suited for use in liquid chromatography to separate out hydrophilic substances because it contains the porous resin particles of the present invention.

Advantageous Effects of the Invention

The present invention provides porous resin particles with high water absorbance and high oil absorbance, a method of manufacturing the porous resin particles, and a dispersion liquid, medicinal-ingredient-containing particles, an external preparation, a coating material, a light diffusion member, and a liquid-chromatography separating agent that contain the porous resin particles.

DESCRIPTION OF EMBODIMENTS

Figure 1:
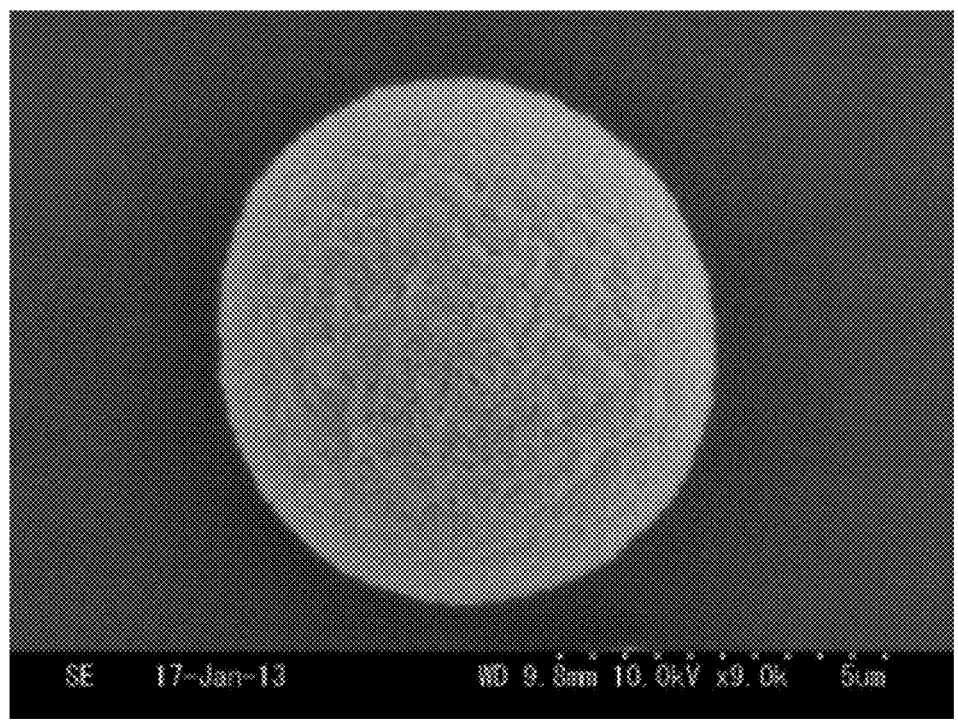
FIG. 1 is a scanning electron microscope (SEM) image of porous resin particles in accordance with Example 1 of the present invention.

The following will be described the present invention in detail.

Porous Resin Particles

The porous resin particles of the present invention contain a polymer of a monomer mixture. The monomer mixture in turn contains a mono(meth)acrylate-based monomer and a polyfunctional vinyl-based monomer. The mono(meth)acrylate-based monomer contains: an ethylenic unsaturated group only in a (meth)acrylic acid residue; a hydroxyl group in an alcohol residue; and at least one of an ether group and an ester group in an alcohol residue. The polyfunctional vinyl-based monomer contains two or more ethylenic unsaturated groups. In addition, the porous resin particles of the present invention have a water absorption value of from more than 400 ml to 700 ml per 100 g of the particles and an oil absorption value of from more than 400 ml to 700 ml per 100 g of the particles.

The quantification, as well as the qualitative and other related analysis, of the structural unit derived from each monomer for the porous resin particles of the present invention may be checked by gas chromatography, liquid chromatography, infrared (IR) spectroscopy, nuclear magnetic resonance (NMR) spectroscopy, or any other publicly known analytical method. The weight ratio of monomers in the monomer mixture is substantially equal to the weight ratio of the structural units derived from those monomers in the porous resin particles of the present invention.

Mono(meth)acrylate-Based Monomer

The porous resin particles of the present invention contain structural units derived from the mono(meth)acrylate-based monomer described above.

The mono(meth)acrylate-based monomer is an ester formed by a (meth)acrylic acid residue and an alcohol residue and contains: an ethylenic unsaturated group only in a (meth)acrylic acid residue; a hydroxyl group in an alcohol residue; and at least one of an ether group and an ester group in an alcohol residue. The mono(meth)acrylate-based monomer may be any publicly known mono(meth)acrylate-based monomer containing: an ethylenic unsaturated group only in a (meth)acrylic acid residue; a hydroxyl group in an alcohol residue; and at least one of an ether group and an ester group in an alcohol residue as long as that monomer does not affect the water and oil absorbance of the porous resin particles. The mono(meth)acrylate-based monomer is preferably a mono(meth)acrylic acid ester containing an aliphatic hydrocarbon group as a hydrocarbon group in its alcohol residue (aliphatic mono(meth)acrylate-based monomer). The ether group may be, for example, a group derived from ethylene glycol (an oxyethylene group having an oxygen atom bonded to a carbon atom) or a group derived from propylene glycol (an oxypropylene group having an oxygen atom bonded to a carbon atom). The ester group may be a group derived from lactone (an oxycarbonyl alkylene group having an oxygen atom bonded to a carbon atom).

From that viewpoint, the mono(meth)acrylate-based monomer is preferably, in particular, a compound of either general formula (1) or general formula (2):

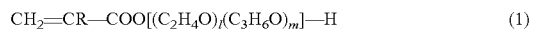
$$CH_2=CR-COO[(C_2H_4O)_l(C_3H_6O)_m]-H \qquad (1)$$

where R is either H or $CH_3$, l is 0 to 50, m is 0 to 50, and l+m>1, and

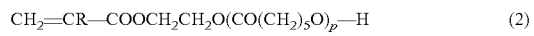
$$CH_2=CR-COOCH_2CH_2O(CO(CH_2)_5O)_p-H \qquad (2)$$

where R is either H or $CH_3$, and p is 1 to 50.

In the compound of general formula (1), if l is greater than 50, the porous resin particles have a lower porosity, hence possibly leading to insufficient water and oil absorbance, and have less polymerization stability, possibly resulting in coalescence and poor redispersibility of the porous resin particles. In the compound of general formula (1), if m is greater than 50, the porous resin particles have a lower porosity, hence possibly leading to insufficient water and oil absorbance, and have less polymerization stability, possibly resulting in coalescence and poor redispersibility of the porous resin particles. If l+m is less than or equal to 1, the compound of general formula (1) contains no ether bonds in its alcohol residues. Preferably, l and m range from 1 to 30. More preferably, l and m range from 1 to 7. If l and m are within either of these ranges, the porous resin particles have a sufficient porosity, hence leading to further improvement of water and oil absorbance, and have reduced chances of coalescence and further improved redispersibility. In the compound of general formula (1), the oxyethylene groups and the oxypropylene groups in the compound where l and m are both greater than 1 may reside in blocks (i.e., the same kind of groups may reside next to each other) or in any other sequence as long as the sequence does not affect desirable physical properties.

In the compound of general formula (2), if p is greater than 50, the porous resin particles have a lower porosity, hence possibly leading to insufficient water and oil absorbance, and have less polymerization stability, possibly resulting in coalescence and poor redispersibility of the porous resin particles. Preferably, p ranges from 1 to 30. If p is within this range, the porous resin particles have a sufficient porosity, hence leading to further improvement of water and oil absorbance, and have reduced chances of coalescence and further improved redispersibility.

Either a compound of general formula (1) or a compound of general formula (2) may be used alone; alternatively, two or more of them may be used together.

The mono(meth)acrylate-based monomer may be a commercial product. An exemplary commercial product of the mono(meth)acrylate-based monomer of general formula (1) is the Blemmer® series manufactured by NOF Corporation. Of the Blemmer® series, to name a few examples, Blemmer® 50 PEP-300 (a mixture of compounds of general formula (1) where R is $CH_3$, l is about 3.5 on average, and m is about 2.5 on average), which is a poly(ethylene glycol-propylene glycol) monomethacrylate, and Blemmer® 70 PEP-350B (a mixture of compounds of general formula (1) where R is $CH_3$, l is about 5 on average, and m is about 2 on average), which is a poly(ethylene glycol-propylene glycol) monomethacrylate, are suitable to the present invention. Any one of these commercial products may be used alone; alternatively, two or more of them may be mixed for use.

An exemplary commercial product of the mono(meth) acrylate-based monomer of general formula (2) is the Placcel® FM series manufactured by Daicel Corporation. Of the Placcel® FM series, to name a few examples, Placcel® FM2D (a compound of general formula (2) where R is $CH_3$, and p is 2) and Placcel® FM3 (a compound of general formula (2) where R is $CH_3$, and p is 3) are suitable to the present invention. Any one of these commercial products may be used alone; alternatively, two or more of them may be mixed for use.

The mono(meth)acrylate-based monomer is preferably used in an amount of from 2 wt % to less than 30 wt % as based on the total amount of the monomer mixture. If the mono(meth)acrylate-based monomer is used in an amount of less than 2 wt % as based on the total amount of the monomer mixture, the porous resin particles have less affinity for a hydrophilic dispersion medium, hence possibly resulting in a lower water absorption value, and may fail to exhibit sufficient redispersibility in the hydrophilic dispersion medium. On the other hand, if the mono(meth)acrylate-based monomer is used in an amount of more than 30 wt % as based on the total amount of the monomer mixture, the porous resin particles have a lower porosity, hence possibly resulting in lower water and oil absorption values, and may have insufficient redispersibility in a hydrophilic dispersion medium. The mono(meth)acrylate-based monomer is used in an amount of more preferably from 5 wt % to 20 wt %, and even more preferably from 5 wt % to 10 wt %, as based on the total amount of the monomer mixture. These ranges further improve the water and oil absorbance and redispersibility of the porous resin particles in the hydrophilic dispersion medium.

Polyfunctional Vinyl-Based Monomer

The porous resin particles of the present invention contain structural units derived from a polyfunctional vinyl-based monomer containing two or more ethylenic unsaturated groups. The polyfunctional vinyl-based monomer may be any publicly known polyfunctional vinyl-based monomer containing two or more ethylenic unsaturated groups as long as the monomer does not affect the water and oil absorbance of the porous resin particles of the present invention.

Examples of the polyfunctional vinyl-based monomer include polyfunctional (meth)acrylate-based monomers that contain two or more ethylenic unsaturated groups and aromatic divinyl-based monomers.

Examples of the polyfunctional (meth)acrylate-based monomer include ethylene glycol di(meth)acrylate, diethylene glycol di(meth)acrylate, triethylene glycol di(meth) acrylate, tetraethylene glycol di(meth)acrylate, nonaethylene glycol di(meth)acrylate, tetradecaethylene glycol di(meth)acrylate, decaethylene glycol di(meth)acrylate, pentadecaethylene glycol di(meth)acrylate, 1,3-butylene glycol di(meth)acrylate, 1,4-butanediol di(meth)acrylate, 1,6-hexanediol di(meth)acrylate, glycerin di(meth)acrylate, trimethylolpropane tri(meth)acrylate, pentaerythritol tetra (meth)acrylate, phthalate diethylene glycol di(meth)acrylate, caprolactone-modified dipentaerythritol hexa(meth) acrylate, caprolactone-modified neopentyl glycol hydroxypivalate diacrylate, polyester acrylate, and urethane acrylate.

Examples of the aromatic divinyl-based monomer include divinyl benzene, divinyl naphthalene, and their derivatives.

Any one of these polyfunctional vinyl-based monomers may be used alone; alternatively, two or more of them may be combined for use. Of the polyfunctional vinyl-based monomers described above, ethylene glycol di(meth)acrylate is excellent in improving the water and oil absorbance of the porous resin particles. Therefore, the polyfunctional vinyl-based monomer preferably contains ethylene glycol di(meth)acrylate.

The polyfunctional vinyl-based monomer is used in an amount of preferably from more than 70 wt % to 98 wt % as based on the total amount of the monomer mixture. If the polyfunctional vinyl-based monomer is used in an amount of less than 70 wt % as based on the total amount of the monomer mixture, the porous resin particles have a lower porosity, hence possibly leading to insufficient water and oil absorbance. On the other hand, if the polyfunctional vinyl-based monomer is used in an amount of more than 98 wt % as based on the total amount of the monomer mixture, the porous resin particles have less affinity for a hydrophilic dispersion medium, hence possibly resulting in a lower water absorption value, and may fail to exhibit sufficient redispersibility in the hydrophilic dispersion medium. The polyfunctional vinyl-based monomer is used in an amount of more preferably from 75 wt % to 95 wt % as based on the total amount of the monomer mixture. This range further improves the water and oil absorbance.

Other Monofunctional Vinyl-Based Monomers

The porous resin particles of the present invention may further contain structural units derived from another monofunctional vinyl-based monomer containing a single ethylenic unsaturated group. This other monofunctional vinyl-based monomer may be any publicly known monofunctional vinyl-based monomer, except for the mono(meth)acrylate-based monomer described above, containing a single ethylenic unsaturated group as long as that monomer does not affect the water and oil absorbance of the porous resin particles of the present invention.

Examples of the other monofunctional vinyl-based monomer include (meth)acrylates, alkyl(meth)acrylate-based monomers, 2-hydroxyethyl methacrylate, 2-methoxyethyl methacrylate, glycidyl methacrylate, tetrahydrofurfuryl methacrylate, diethylaminoethyl methacrylate, trifluoroethyl methacrylate, heptadecafluorodecyl methacrylate, styrene-based monomers, and vinyl acetate. Of these other monofunctional vinyl-based monomers, alkyl(meth)acrylate-based monomers are excellent in improving the redispersibility of the porous resin particles. Therefore, the other monofunctional vinyl-based monomer preferably contains an alkyl(meth)acrylate-based monomer.

The alkyl group in the alkyl(meth)acrylate-based monomer may be straight chained or branched. Examples of the alkyl(meth)acrylate-based monomer include alkyl acrylates, such as methyl acrylate, ethyl acrylate, n-butyl acrylate, isobutyl acrylate, and 2-ethylhexyl acrylate; and alkyl methacrylates, such as n-butyl methacrylate, 2-ethylhexyl methacrylate, methyl methacrylate, ethyl methacrylate, isobutyl methacrylate, cyclohexyl methacrylate, benzyl methacrylate, and isobornyl methacrylate. The alkyl group in the alkyl(meth)acrylate-based monomer is preferably a $C_1$-$C_8$ alkyl group and more preferably a $C_1$-$C_4$ alkyl group. If the alkyl group in the alkyl(meth)acrylate-based monomer contains 1 to 8 carbon atoms, the porous resin particles have more affinity for the hydrophilic dispersion medium, hence exhibiting improved water absorbance and redispersibility in the hydrophilic dispersion medium. The other monofunctional vinyl-based monomer preferably contains methyl methacrylate to obtain porous resin particles that have very good water and oil absorbance and very good redispersibility in the hydrophilic dispersion medium.

Examples of the styrene-based monomer include styrene, p-methylstyrene, and α-methylstyrene.

Any one of these other monofunctional vinyl-based monomers may be used alone; alternatively, two or more of them may be combined for use.

The other monofunctional vinyl-based monomer is used in an amount of from 0 wt % to 20 wt % as based on the total amount of the monomer mixture. Even if the other monofunctional vinyl-based monomer is used in an amount of 0 wt % as based on the total amount of the monomer mixture, that is, even if the monomer mixture contains no other monofunctional vinyl-based monomers, the porous resin particles of the present invention still have high water and oil absorbance. On the other hand, if the other monofunctional vinyl-based monomer is used in an amount of more than 20 wt % as based on the total amount of the monomer mixture, the porous resin particles have a lower porosity, hence possibly leading to insufficient water and oil absorbance. The other monofunctional vinyl-based monomer is used in an amount of more preferably from 3 wt % to 20 wt %, and even more preferably from 5 wt % to 15 wt %, as based on the total amount of the monomer mixture. These ranges further improve the water and oil absorbance.

The porous resin particles of the present invention have a plurality of pores (in other words, the particles are porous) with a pore diameter of preferably from 4 nm to 20 nm and more preferably from 4 nm to 15 nm. If the pore diameter is less than 4 nm, the water and oil absorbance may be insufficient. If the pore diameter is more than 20 nm, the light scattering effects may be insufficient. In the present invention, the pore diameter refers to the pore diameter (average pore diameter) obtained by the BJH method from nitrogen desorption isotherm, for example, the pore diameter (average pore diameter) obtained from measurements by a pore diameter measuring method which will be described later in detail in the examples of the invention.

The porous resin particles of the present invention have a specific surface area of preferably from 3 $m^2/g$ to 500 $m^2/g$, more preferably from 5 $m^2/g$ to 500 $m^2/g$, and even more preferably from 8 $m^2/g$ to 500 $m^2/g$. If the porous resin particles have a specific surface area of less than 3 $m^2/g$, the water and oil absorbance, hence the light scattering effects, may be insufficient. On the other hand, if the porous resin particles have a specific surface area of more than 500 $m^2/g$, the porous resin particles are no longer spherical: if such porous resin particles are blended in an external preparation, the external preparation may show less spreading and slippage when applied to the skin; if the porous resin particles are blended in a coating material, the coating film formed from the coating material may likely have bumps (projections).

The specific surface area refers to the surface area per unit weight and in the present invention refers to the specific surface area obtained by the BET method ($N_2$). The method of measuring the specific surface area by the BET method ($N_2$) will be described in the examples of the invention.

The porous resin particles of the present invention have a volume-average particle diameter of preferably from 4 μm to 40 μm and more preferably from 4 μm to 20 μm. If the volume-average particle diameter is within these ranges, the porous resin particles of the present invention unfailingly have sufficient surface areas, hence unfailingly exhibiting sufficient water and oil absorbance and sufficient redispersibility in hydrophilic dispersion media.

The porous resin particles of the present invention have a coefficient of variation (CV) of particle diameters of preferably less than or equal to 50% and more preferably less than or equal to 40%. If the particle diameters have a coefficient of variation in these ranges, the external preparation (e.g., cosmetic material) in which the porous resin particles are blended exhibits improved spreading and slippage.

Method of Manufacturing Porous Resin Particles

The porous resin particles of the present invention may be manufactured by a method of manufacturing porous resin particles including the step of suspension-polymerizing a monomer mixture described above in the presence of a non-polymerizable organic solvent as a pore-forming agent, the pore-forming agent being used in the step in an amount of from 200 parts by weight to 500 parts by weight per 100 parts by weight of the monomer mixture.

In the method of manufacturing porous resin particles of the present invention, the suspension polymerization may be carried out by, for example, dispersing droplets of a mixture containing the monomer mixture and the pore-forming agent in an aqueous phase containing an aqueous medium to polymerize the monomer mixture.

The monomer mixture is the one of those explained above and contains the mono(meth)acrylate-based monomer in an amount of from 2 wt % to less than 30 wt % and the polyfunctional vinyl-based monomer in an amount of from more than 70 wt % to 98 wt %. This monomer mixture, as described above, may contain the other monofunctional vinyl-based monomer in an amount of from 0 wt % to 20 wt %.

The non-polymerizable organic solvent as the pore-forming agent may be any publicly known organic solvent that renders porous the resin particles obtained by the manufacturing method described above and that does not polymerize with the monomer mixture. Examples of the non-polymerizable organic solvent include aromatic compounds, such as toluene and benzene; acetate ester-based compounds, such as ethyl acetate and butyl acetate; and saturated aliphatic hydrocarbons, such as n-hexane, cyclohexane, n-octane, and n-dodecane. Any one of these non-polymerizable organic solvents may be used alone; alternatively, two or more of them may be combined for use.

Of the non-polymerizable organic solvents above, acetate esters are excellent in rendering porous the resin particles obtained by the manufacturing method described above. Therefore, the pore-forming agent is preferably an acetate ester and more preferably ethyl acetate.

The pore-forming agent is used in an amount of preferably from 200 parts by weight to 500 parts by weight, and more preferably from 200 parts by weight to 400 parts by weight, per 100 parts by weight of the monomer mixture. If the pore-forming agent is used in an amount of less than 200 parts by weight, the resultant resin particles may not be sufficiently porous to exhibit desirable water and oil absorbance. On the other hand, if the pore-forming agent is used in an amount of more than 500 parts by weight, the monomer mixture may not form droplets during suspension polymerization of the monomer mixture.

The aqueous medium is by no means limited and may be, for example, water or a mixed medium of water and a water-soluble organic medium (methanol, ethanol, or another lower alcohol (alcohol containing less than or equal to 5 carbon atoms)). The aqueous medium is typically used in an amount of from 100 parts by weight to 1,000 parts by weight per 100 parts by weight of the monomer mixture to stabilize the resin particles.

The suspension polymerization is carried out preferably in the presence of at least one of an anionic surfactant and a zwitterionic surfactant, and more preferably in the presence of both an anionic surfactant and a zwitterionic surfactant, to manufacture desirable porous resin particles in a more stable manner. For example, preferably, at least one of an anionic surfactant and a zwitterionic surfactant is added to an aqueous phase containing the aqueous medium. More preferably, both the anionic surfactant and the zwitterionic surfactant are added to an aqueous phase containing the aqueous medium.

The anionic surfactant may be any publicly known anionic surfactant that is used in the manufacture of resin particles. Examples of the anionic surfactant include fatty acid soaps, such as sodium oleate and castor oil potassium soap; alkyl sulfate salts, such as sodium lauryl sulfate and ammonium lauryl sulfate; alkylbenzene sulfonate, such as sodium dodecyl benzene sulfonate; alkyl naphthalene sulfonic acid salts; alkane sulfonic acid salts; dialkyl sulfosuccinic acid salts, such as dioctyl sodium sulfosuccinate; phosphate ester salts, such as sodium polyoxyethylene alkyl phenyl ether phosphate and sodium polyoxyalkylene aryl ether phosphate; naphthalene sulfonate formalin condensate; polyoxyethylene alkyl phenyl ether sulfate salts; and polyoxyethylene alkyl sulfate salts. Any one of these anionic surfactants may be used alone; alternatively, two or more of them may be combined for use.

The anionic surfactant is used in an amount of preferably from 0.005 parts by weight to 0.1 parts by weight, and more preferably from 0.01 parts by weight to 0.05 parts by weight, per 100 parts by weight of the aqueous medium. If the anionic surfactant is used in an amount of less than 0.005 parts by weight per 100 parts by weight of the aqueous medium, the monomer mixture may not readily form small droplets, which could hinder the manufacture of desirable porous resin particles with high water and oil absorbance. On the other hand, if the anionic surfactant is used in an amount of more than 0.1 parts by weight, fine resin particles may form in large quantities, which could hinder the manufacture of desirable porous resin particles with high water and oil absorbance.

The zwitterionic surfactant may be any publicly known zwitterionic surfactant that is used in the manufacture of resin particles. Examples of the zwitterionic surfactant include lauryl dimethylamine oxide, betaine lauryl dimethylamino acetate, phosphate ester-based surfactants, and phosphite ester-based surfactants. Any one of these zwitterionic surfactants may be used alone; alternatively, two or more of them may be combined for use.

The zwitterionic surfactant is used in an amount of preferably from 0.01 parts by weight to 0.1 parts by weight, and more preferably from 0.02 to 0.05 parts by weight, per 100 parts by weight of the aqueous medium. If the zwitterionic surfactant is used in an amount of less than 0.01 parts by weight, particles may aggregate over the course of polymerization, which could hinder the manufacture of desirable porous resin particles with high water and oil absorbance. On the other hand, if the zwitterionic surfactant is used in an amount of more than 0.1 parts by weight, fine resin particles may form in large quantities, which could hinder the manufacture of desirable porous resin particles with high water and oil absorbance.

The polymerization temperature for the monomer mixture is preferably in a range from 30° C. to 105° C. This polymerization temperature is preferably maintained for a period of from 0.1 hours to 20 hours. When the polymerization is completed, a suspension (slurry) is obtained that contains porous resin particles that in turn contain a pore-forming agent in the particles. The suspension is distilled to remove the pore-forming agent. Preferably, after the dispersion stabilizer in the suspension is dissolved and removed, for example, with an acid, the porous resin particles are filtered out to remove the aqueous medium, washed in water or in a solvent, and then dried, to isolate the porous resin particles.

In the suspension polymerization, typically, a polymerization initiator is added to the monomer mixture. Examples of the polymerization initiator include peroxides, such as benzoyl peroxide, lauroyl peroxide, tert-butyl peroxyisobutyrate; azo compounds, such as 2,2'-azobisisobutyronitrile, 2,2'-azobis(2,4-dimethylvaleronitrile), and 2,2'-azobis-(2-methylpropionate); and peroxide salts, such as potassium persulfate and ammonium persulfate. Any one of these polymerization initiators may be used alone; alternatively, two or more of them may be combined for use.

The polymerization initiator is used in an amount of preferably from 0.01 parts by weight to 10 parts by weight, and more preferably from 0.01 parts by weight to 5 parts by weight, per 100 parts by weight of the monomer mixture. If the polymerization initiator is used in an amount of less than 0.01 parts by weight per 100 parts by weight of the monomer mixture, the polymerization initiator does not readily react to initiate polymerization. On the other hand, if the polymerization initiator is used in an amount of more than 10 parts by weight per 100 parts by weight of the monomer mixture, its cost performance is low.

In the suspension polymerization, the aqueous phase preferably contains a dispersion stabilizer to manufacture desirable porous resin particles in a more stable manner. Examples of the dispersion stabilizer include inorganic oxides, such as silica and zirconium oxide; poorly water-soluble salts, such as barium carbonate, calcium carbonate, tribasic calcium phosphate, magnesium pyrophosphate, and calcium sulfate; and inorganic polymer substances, such as talc, bentonite, silicic acid, kieselguhr, and clay. Of these dispersion stabilizers, a preferred one is magnesium pyrophosphate prepared by double decomposition to obtain porous resin particles with consistent particle diameters (especially, those with a coefficient of variation of particle diameters of less than or equal to 40%).

The dispersion stabilizer is used in an amount of preferably from 0.1 parts by weight to 20 parts by weight, and more preferably from 0.5 parts by weight to 10 parts by weight, per 100 parts by weight of the monomer mixture. If the dispersion stabilizer is used in an amount of more than 20 parts by weight, the suspension may have too great viscosity to flow. On the other hand, if the dispersion stabilizer is used in an amount of less than 0.1 parts by weight, the porous resin particles may disperse insufficiently and coalesce.

To obtain porous resin particles with more consistent particle diameters, before the suspension polymerization, droplets may be dispersed in a microfluidizer, a nanomizer, or another like high pressure disperser that exploits mutual collisions of droplets and collisional force exerted by disperser walls for better dispersion.

Dispersion Liquid

The dispersion liquid of the present invention contains the porous resin particles and the hydrophilic dispersion medium, both described earlier. Since the porous resin particles of the present invention have excellent redispersibility, the dispersion liquid containing the porous resin particles of the present invention and the hydrophilic dispersion medium has excellent redispersibility.

The at least one hydrophilic dispersion medium selected from the group consisting of water and alcohols for use in the dispersion liquid of the present invention is by no means limited in any particular manner; examples include water, ethanol, 1-propanol, 2-propanol, glycerin, propylene glycol, and 1,3-butylene glycol. Any one of these hydrophilic dispersion media may be used alone; alternatively, two or more of them may be mixed for use. The hydrophilic dispersion medium typically accounts for 20 wt % to 90 wt % of the dispersion liquid.

The dispersion liquid of the present invention may contain, apart from the porous resin particles and the hydrophilic dispersion media, oils, powders (pigments), fluorine compounds, surfactants, mucilaginous agents, preservatives, fragrances, ultraviolet protecting agents (both organic and inorganic, and may offer protection for either UV-A or UV-B), salts, solvents other than the hydrophilic dispersion media, antioxidants, chelating agents, neutralizers, pH-adjusters, insect repellents, medicinal ingredients, pigments, and various other components.

The dispersion liquid of the present invention may contain small quantities of other resin components as long as they do not affect redispersibility and other desirable physical properties. Specific examples of the other resin components include vinyl chloride-based resins, such as vinyl chloride polymers and vinyl chloride-vinylidene chloride copolymers; vinyl ester-based resins, such as vinyl acetate polymers and vinyl acetate-ethylene copolymers; styrene-based resins, such as styrene polymers, styrene-acrylonitrile copolymers, styrene-butadiene-acrylonitrile copolymers, styrene-butadiene block copolymers, styrene-isoprene block copolymers, and styrene-methyl methacrylate copolymers; and (meth)acrylate ester-based resins, such as (meth)acrylic-based resins, (meth)acrylate ester-acrylonitrile copolymers, and (meth)acrylate ester-styrene copolymers.

Since the porous resin particles of the present invention have excellent redispersibility, a uniform dispersion liquid is readily obtainable by, for example, gentle mixing in a publicly known mixer, a disperser, or another like dispersing means.

External Preparation

The external preparation of the present invention contains the porous resin particles. Since the external preparation of the present invention has high water absorbance and high oil absorbance, it absorbs sweat and sebum and keeps the skin smooth and silky when applied to the skin. In addition, even if the porous resin particles have precipitated on the bottom of the container, the external preparation of the present invention becomes usable by shaking lightly before use because the external preparation has excellent redispersibility in the hydrophilic dispersion medium. Furthermore, since the porous resin particles have good dispersibility in the hydrophilic dispersion medium, the external preparation of the present invention exhibits excellent application properties and spreadability on the skin. The external preparation of the present invention is also advantageous for manufacturing in that the porous resin particles are readily dispersible in manufacturing.

The porous resin particle content of the external preparation of the present invention may be suitably specified according to the type of the external preparation, and is preferably from 1 wt % to 80 wt % and more preferably from 3 wt % to 70 wt %. If the porous resin particle content of the entire external preparation is less than 1 wt %, the porous resin particles may not produce appreciable effects. On the other hand, if the porous resin particle content is more than 80 wt %, the extra content may not produce rewarding, noticeable effects, which is not cost-effective.

The external preparation of the present invention may be used, for example, as an external medicine or as a cosmetic material. The external medicine is by no means limited in any particular manner as long as it is applicable to the skin. Specific examples of the external medicine include cream, ointment, and emulsion. Specific examples of the cosmetic material include cleansing cosmetics, such as soap, body shampoo, facial cleansing cream, scrub cleanser, and toothpaste; makeup cosmetic materials, such as makeup powder, face powder (e.g., loose powder and pressed powder), makeup foundation (e.g., powder foundation, liquid foundation, and emulsion foundation), lipstick, lip balm, cheek color, eye makeup cosmetics, and nail polish; lotion preparations, such as pre-shave lotions and body lotions; external preparations for the body, such as body powder and baby powder; skin care products, such as skin lotion, cream, and milky lotion (cosmetic milky lotion); antiperspirants (e.g., liquid antiperspirants, solid antiperspirants, and cream antiperspirants); skin packs; hair-washing cosmetics; hair-coloring preparations; hairdressing agents; fragrances; bath preparations; sunscreen agents; sun tanning agents; and shaving cream.

Of these external preparations, makeup powder, face powder, powder foundation, body powder, baby powder, and other like powder-based cosmetic materials (in other words, powdery cosmetic materials) are suitable applications for the porous resin particles of the present invention because they show excellent water and oil absorbance if the porous resin particles are used in them.

Body shampoo, pre-shave lotion, body lotion, and other like dispersion liquid-based cosmetic materials are suitable external preparation applications for the porous resin particles of the present invention because they show excellent water and oil absorbance and excellent dispersibility if the porous resin particles are used in them.

The porous resin particles to be blended in the external preparation of the present invention may be treated with an oil; a surface treatment agent, such as a silicone compound or a fluorine compound; organic powder; or inorganic powder.

The oil may be any oil that is commonly used in external preparations. Examples of the oil include hydrocarbon oils, such as liquid paraffin, squalane, petrolatum, and paraffin wax; higher fatty acids, such as lauric acid, myristic acid, palmitic acid, stearic acid, oleic acid, behenic acid, undecylenic acid, hydroxystearic acid, linoleic acid, lanolin fatty acid, and synthetic fatty acid; ester oils, such as glyceryl trioctanoate, propylene glycol dicaprate, cetyl 2-ethylhexanoate, and isocetyl stearate; waxes, such as beeswax, spermaceti, lanolin, carnauba wax, and candelilla wax; fats and oils, such as linseed oil, cottonseed oil, castor oil, egg-yolk oil, and coconut oil; metal soaps, such as zinc stearate and zinc laurate; and higher alcohols, such as cetyl alcohol, stearyl alcohol, and oleyl alcohol. The porous resin particles may be treated with the oil by any method that is by no means limited in any particular manner. An example of such a method is a dry method in which oil is added to the porous resin particles, and the mixture is stirred in a mixer to coat the porous resin particles with the oil. Another example is a wet method in which oil is heated and dissolved in ethanol, propanol, ethyl acetate, hexane, or another appropriate solvent, the porous resin particles are added to the dissolved oil and mixed while stirring, and thereafter the solvent is removed under reduced pressure or by heating to coat the porous resin particles with the oil.

The silicone compound may be any compound that is commonly used in external preparations. Examples of the silicone compound include dimethylpolysiloxane, methylhydrogenpolysiloxane, methylphenylpolysiloxane, acrylsilicone graft polymers, organic silicone resin, and partially crosslinked organopolysiloxane polymers. The porous resin particles may be treated with the silicone compound by any method that is by no means limited in any particular manner. Examples of such a method include the dry and wet methods described above. The silicone compound may be subjected to firing where necessary. For a reactive silicone compound, a reaction catalyst, as an example, may be added where appropriate.

The fluorine compound may be any compound that is commonly blended in external preparations. Examples of the fluorine compound include perfluoroalkyl group-containing esters, perfluoroalkyl silane, perfluoropolyethers, and perfluoro group-containing polymers. The porous resin particles may be treated with the fluorine compound by any method that is by no means limited in any particular manner. Examples of such a method include the dry and wet methods described above. The fluorine compound may be subjected to firing where necessary. For a reactive fluorine compound, a reaction catalyst, as an example, may be added where appropriate.

Examples of the organic powder include natural macromolecular compounds, such as gum arabic, gum tragacanth, guar gum, locust bean gum, karaya gum, Irish moss, Quince seeds, gelatins, shellac, rosin, and casein; semisynthetic macromolecular compounds, such as sodium carboxymethyl cellulose, hydroxyethyl cellulose, methyl cellulose, ethyl cellulose, sodium alginate, gum ester, nitrocellulose, hydroxypropyl cellulose, and crystalline cellulose; polyvinyl alcohol; polyvinylpyrrolidone; sodium polyacrylate; carboxyvinyl polymers; polyvinyl methylether; polyamide resins; silicone oil; and resin particles, such as nylon particles, polymethyl methacrylate particles, crosslinked polystyrene particles, silicone-based particles, polyurethane particles, polyethylene particles, and fluororesin particles. Examples of the inorganic powder include iron oxides, ultramarines, ferric ferrocyanide, chromium oxides, chromium hydroxide, carbon black, manganese violet, titanium oxides, zinc oxides, talc, kaolin, calcium carbonate, magnesium carbonate, mica, aluminum silicate, barium silicate, calcium silicate, magnesium silicate, silica, zeolite, barium sulfate, calcined calcium sulfate (calcined gypsum), calcium phosphate, hydroxyapatite, and ceramic powder. Any one of these organic and inorganic powders may be surface-treated in advance. Examples of the surface treatment include any publicly known surface treatment technology described earlier.

A commonly used main agent or additives may be blended with the external preparation of the present invention where necessary as long as they do not negatively affect the effects of the present invention. Examples of the main agent and additives include water, lower alcohols (alcohols with less than or equal to 5 carbon atoms), fats and oils, waxes, hydrocarbons, higher fatty acids, higher alcohols, sterols, fatty acid esters, metal soaps, moisturizing agents, surfactants, macromolecular compounds, color ingredients, fragrances, clay minerals, antiseptics, anti-inflammatory agents, antioxidants, ultraviolet absorbers, organic and inorganic composite particles, pH-adjusters (e.g., triethanolamine), specially mixed additives, and pharmaceutically active ingredients.

Specific examples of the fats and oils and waxes include avocado oil, almond oil, olive oil, cacao butter, beef tallow, sesame oil, wheat germ oil, safflower oil, shea butter, turtle oil, *camellia* oil, persic oil, castor oil, grape seed oil, macadamia nut oil, mink oil, egg-yolk oil, Japan wax, coconut oil, rose hip oil, hardened oil, silicone oil, orange roughy oil, carnauba wax, candelilla wax, spermaceti, jojoba oil, montan wax, beeswax, and lanolin.

Specific examples of the hydrocarbon include liquid paraffin, petrolatum, paraffin, ceresin, microcrystalline wax, and squalane.

Specific examples of the higher fatty acid include fatty acids with 11 or more carbon atoms, such as lauric acid, myristic acid, palmitic acid, stearic acid, oleic acid, behenic acid, undecylenic acid, hydroxystearic acid, linoleic acid, lanolin fatty acid, and synthetic fatty acid.

Specific examples of the higher alcohol include alcohols with 6 or more carbon atoms, such as lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, isostearyl alcohol, jojoba alcohol, and decyltetradecanol.

Specific examples of the sterol include cholesterol, dihydrocholesterol, and phytocholesterol.

Specific examples of the fatty acid ester include linoleic acid esters, such as ethyl linoleate; lanolin fatty acid esters, such as lanolin fatty acid isopropyl ester; lauric acid esters, such as hexyl laurate; myristic acid esters, such as isopropyl myristate, myristyl myristate, cetyl myristate, and octyldodecyl myristate; oleic acid esters, such as decyl oleate and octyldodecyl oleate; dimethyl octanoic acid esters, such as hexyldecyl dimethyloctanoate; isooctanoic acid esters, such as cetyl isooctanoate (cetyl 2-ethylhexanoate); palmitic acid esters, such as decyl palmitate; and cyclic alcohol fatty acid esters, such as glycerin trimyristate, glycerin tri(capryl caprate), propylene glycol dioleate, glycerin triisostearate, glycerin triisooctanoate, cetyl lactate, myristyl lactate, diisostearyl malate, cholesteryl isostearate, and cholesteryl 12-hydroxystearate.

Specific examples of the metal soap include zinc laurate, zinc myristate, magnesium myristate, zinc palmitate, zinc stearate, aluminum stearate, calcium stearate, magnesium stearate, and zinc undecylenate.

Specific examples of the moisturizing agent include glycerin, propylene glycol, 1,3-butylene glycol, polyethylene glycol, sodium dl-pyrrolidonecarboxylate, sodium lactate, sorbitol, sodium hyaluronate, polyglycerin, xylitol, and maltitol.

Specific examples of the surfactant include anionic surfactants, such as higher fatty acid soaps, higher alcohol sulfate esters, N-acyl glutamic acid salts, and phosphate ester salts; cationic surfactants, such as amine salts and quaternary ammonium salts; zwitterionic surfactants, such as betaine-type zwitterionic surfactants, amino acid-type zwitterionic surfactants, imidazoline-type zwitterionic surfactants, and lecithin; and non-ionic surfactants, such as fatty acid monoglyceride, polyethylene glycol, propylene glycol fatty acid ester, sorbitan fatty acid ester, sucrose fatty acid ester, polyglycerol fatty acid ester, and ethylene oxide condensates.

Specific examples of the macromolecular compound include natural macromolecular compounds, such as gum arabic, gum tragacanth, guar gum, locust bean gum, karaya gum, Irish moss, Quince seed, gelatin, shellac, rosin, and casein; semisynthetic macromolecular compounds, such as sodium carboxymethyl cellulose, hydroxyethyl cellulose, methyl cellulose, ethyl cellulose, sodium alginate, gum ester, nitrocellulose, hydroxypropyl cellulose, and crystalline cellulose; synthetic macromolecular compounds, such as polyvinyl alcohols, polyvinylpyrrolidone, sodium polyacrylate, carboxyvinyl polymers, polyvinyl methylether, polyamide resins, and silicone oil; and resin particles, such as nylon particles, poly(meth)acrylate particles (e.g., polymethyl methacrylate particles), polystyrene particles, silicone-based particles, polyurethane particles, polyethylene particles, and silica particles.

Specific examples of the color ingredient include inorganic pigments, such as iron oxides (e.g., red, yellow, and black iron oxides), ultramarines, ferric ferrocyanide, chromium oxide, chromium hydroxide, carbon black, manganese violet, titanium oxide, zinc oxide, talc, kaolin, calcium carbonate, magnesium carbonate, mica, aluminum silicate, barium silicate, calcium silicate, magnesium silicate, silica, zeolite, barium sulfate, calcined calcium sulfate (calcined gypsum), calcium phosphate, hydroxyapatite, and ceramic powder; and tar dyes, such as azo-based dyes, nitro-based dyes, nitroso-based dyes, xanthene-based dyes, quinoline-based dyes, anthraquinoline-based dyes, indigo-based dyes, triphenylmethane-based dyes, phthalocyanine-based dyes, and pyrene-based dyes.

The ingredient powder for macromolecular compounds and the ingredient powder for color materials may be surface-treated in advance before use. The surface treating method may be any publicly known surface treatment technology. Examples of the treatment include treatments with an oil, such as hydrocarbon oil, ester oil, or lanolin; treatments with a silicone, such as dimethylpolysiloxane, methylhydrogenpolysiloxane, or methylphenylpolysiloxane; treatments with a fluorine compound, such as perfluoroalkyl group-containing ester, perfluoroalkyl silane, perfluoropolyether, or perfluoroalkyl group-containing polymer; treatments with a silane coupling agent, such as 3-methacryloxypropyltrimethoxysilane, or 3-glycidoxypropyltrimethoxysilane; treatments with a titanium coupling agent, such as isopropyl triisostearoyl titanate or isopropyl tris(dioctylpyrophosphate) titanate; treatments with a metal soap; treatments with an amino acid, such as acyl glutamic acid; treatments with lecithin, such as hydrogenated egg-yolk lecithin; treatments with collagen; treatments with polyethylene; moisturizing treatments; treatments with an inorganic compound; and mechanochemical treatments.

Specific examples of the clay mineral include components that have several functions including those of extender pigments and adsorbents, such as talc, mica (e.g., white mica), sericite, titanium sericite (titanium oxide-coated sericite), and Veegum® manufactured by Vanderbilt.

Specific examples of the fragrance include anisaldehyde, benzyl acetate, and geraniol. Specific examples of the antiseptics include methylparaben, ethylparaben, propylparaben, benzalkonium, and benzethonium. Specific examples of the antioxidants include dibutylhydroxytoluene, butylhydroxyanisole, propyl gallate, and tocopherol. Specific examples of the ultraviolet absorbers include inorganic absorbents, such as fine particles of titanium oxide, fine particles of zinc oxide, fine particles of cerium oxide, fine particles of iron oxide, and fine particles of zirconium oxide; and organic absorbents, such as benzoic acid-based absorbents, para-aminobenzoic acid-based absorbents, anthranilic acid-based absorbents, salicylic acid-based absorbents, cinnamic acid-based absorbents, benzophenone-based absorbents, and dibenzoyl methane-based absorbents.

Specific examples of the specially mixed additive include hormones, such as estradiol, estrone, ethinylestradiol, cortisone, hydrocortisone, and prednisone; vitamins, such as vitamin A, vitamin B, vitamin C, and vitamin E; skin astringents, such as citric acid, tartaric acid, lactic acid, aluminum chloride, aluminum potassium sulfate, allantoin chlorohydroxy aluminum, zinc para-phenolsulfonate, and zinc sulfate; trichogenous accelerants, such as cantharides tincture, *Capsicum* tincture, ginger tincture, *swertia* extract, garlic extract, hinokitiol, carpronium chloride, glyceride pentadecanoate, vitamin E, estrogen, and photosensitive elements; and whitening agents, such as magnesium L-ascorbyl-phosphate, and kojic acid.

Medicinal-Ingredient-Containing Particles

The medicinal-ingredient-containing particles of the present invention contain the porous resin particles described above and a medicinal ingredient.

Examples of the medicinal ingredient may be any ingredient used conventionally in pharmaceuticals, quasi-drugs, and cosmetics.

Specific examples of the medicinal ingredient include *Angelica keiskei* extract, *Persea gratissima* (avocado) fruit extract, *Hydrangea serrata* leaf extract, *Althaea officinalis* extract, *Arnica montana* extract, apricot extract, apricot kernel extract, *Foeniculum vulgare* extract, *Curcuma longa* (turmeric) extract, *Uuron-cha ekisu* (JTN), *Echinacea angustifolia* leaf extract, *Scutellaria* root extract, *Phellodendron* bark extract, *Hordeum vulgare* extract, *Nasturtium officinale* extract, *Citrus sinensis* extract, dried sea water, hydrolyzed elastin, powdered hydrolyzed *Triticum aestivum*, hydrolyzed silk, *Chamomilla* extract, *Daucus carota sativa* extract, *Artemisia capillaris* extract, *Glycyrrhiza* root extract, *Hibiscus sabdariffa* flower extract, *Actinidia chinensis* (kiwi) fruit extract, *Cinchona* extract, *Cucumis sativus* (cucumber) extract, guanosine, *Sasa veitchii* extract, *Juglans regia* (walnut) extract, *Citrus paradisi* extract, *Clematis* extract, yeast extract, *Arctum lappa* extract, *Symphytum officinale* extract, collagen, *Vaccinium vitis-idaea* extract, *Bupleurum falcatum* Linne extract, umbilical extract, *Salvia* extract, *Saponaria officinalis* leaf/root extract, bamboo grass extract, *Crataegus cuneata* fruit extract, *Lentinus edodes* extract, *Rehmannia glutinosa* extract, *Lithospermum erythrorhizon* root extract, *Shinanoki ekisu* (JTN), *Spiraea ulmaria* flower extract, *Acorus radix* extract, *Shirakaba ekisu* (JTN), *Equisetum arvense* extract, *Lonicera* extract, *Hedera helix* extract, *Crataegus oxyacantha* extract, *Sambucus nigra* extract, *Achillea millefolium* extract, *Mentha piperita* (peppermint) extract, *Malva sylvestris* (mallow) extract, *Swertia* extract, *Taisou ekisu* (JTN), *Thymus vulgaris* (thyme) extract, *Caryophyllus* extract, *Imperata cylindrica* extract, *Chinpi ekisu* (JTN), *Touhi ekisu* (JTN), *Houttuynia cordata* extract, *Lycopersicon esculentum* extract, fermented soybean extract, *Daucus carota* extract, *Rosa canina* fruit extract, *Hibiscus Sabdariffa* flower extract, *Bakumondou ekisu* (JTN), *Petroselinum crispum* extract, honey, *Parietaria Officinalis* extract, *Isodonis japonicus* extract, bisabolol, *Fukitanpopo ekisu* (JTN), *Petasites japonicus* flower extract, *Poria cocos* extract, *Ruscus aculeatus* root extract, *Vitis vinifera* extract, propolis extract, *Luffa cylindrica* extract, *Mentha piperita* extract, *Tilia platyphyllos* flower extract, *Humulus lupulus* (hops) extract, *Pinus sylvestris* cone extract, *Aesculus hippocastanum* extract, *Lysichiton camtschatcense* extract, *Sapindus mukorossi* peel extract, *Prunus persica* extract, *Centaurea cyanus* flower extract, *Yuukari ekisu* (JTN), *Citrus junos* fruit extract, *Yomogi ekisu* (JTN), *Lavandula angustifolia* (lavender) extract, *Malus domestica* extract, *Lactuca sativa* extract, *Citrus limon* (lemon) extract, *Astragalus sinicus* extract, rose extract, *Rosmarinus officinalis* (rosemary) extract, *Anthemis nobilis* extract, and royal jelly extract.

Other specific examples of the medicinal ingredient include biological polymers, such as deoxyribonucleic acid, sodium chondroitin sulfate, collagen, elastin, chitin, chitosan, and hydrolyzed egg shell membrane; moisture retention components, such as amino acid, urea, sodium pyrrolidonecarboxylate, betaine, whey, and trimethyl glycine; oily components, such as sphingolipid, ceramide, cholesterol, cholesterol derivatives, and phospholipid; anti-inflammatory agents, such as ε-aminocaproic acid, glycyrrhizic acid, β-glycyrrhetinic acid, lysozyme chloride, guaiazulen, and hydrocortisones; vitamins, such as vitamin A, vitamin B2, vitamin B6, vitamin D, vitamin E, calcium pantothenate, biotin, and nicotinamide; active ingredients, such as allantoin, diisopropylamine dichloroacetate, and 4-(aminomethyl)cyclohexanecarboxylic acid; antioxidants, such as tocopherol, carotenoid, flavonoid, tannin, lignan, and saponin; blood circulation accelerators, such as γ-oryzanol and vitamin E derivatives; wound healing drugs, such as retinol and retinol derivatives; cepharanthine; Capsicum tincture; hinokitiol; iodized garlic extract; pyridoxine hydrochloride; dl-α-tocopherol; dl-α-tocopherol acetate; nicotinic acid; nicotinic acid derivatives; D-pantothenyl alcohol; acetyl pantothenyl ethylether; biotin; allantoin; isopropyl methyl phenol; estradiol; ethinyl estradiol; carpronium chloride; benzalkonium chloride; diphenhydramine hydrochloride; Quaternium-51; camphor; salicylic acid; vanillylamide nonylate; vanillylamide nonanoate; piroctone olamine; glyceryl pentadecanoate; mono-nitroguaiacol; resorcin; γ-aminobutyric acid; benzethonium chloride; mexiletine hydrochloride; auxin; female hormones; cantharides tincture; ciclosporin; hydrocortisone; polyoxyethylene sorbitan monostearate; analgesic agents; tranquilizers; antihypertensive agents; antibiotics; antihistamines; and antibacterial agents.

Any one of these medicinal ingredients may be used alone; alternatively, two or more of them may be mixed for use.

The medicinal ingredient content of the medicinal-ingredient-containing particles cannot be specified unconditionally because different medicinal ingredients contain different amounts of active ingredient. In general, however, preferred amounts are from 1 part by weight to 300 parts by weight per 100 parts by weight of the porous resin particles, and more preferred amounts are from 5 parts by weight to 200 parts by weight per 100 parts by weight of the porous resin particles.

The medicinal-ingredient-containing particles are prepared by incorporating the medicinal ingredient into the porous resin particles by, for example, kneading the porous resin particles and the medicinal ingredient.

The medicinal-ingredient-containing particles of the present invention may be used as a raw material for an external preparation. In other words, the aforementioned external preparation of the present invention may contain the medicinal-ingredient-containing particles of the present invention. Embodiments of the external preparation containing the medicinal-ingredient-containing particles of the present invention are the same as the embodiments of external preparations described under the heading "External Preparation" above, except that the medicinal-ingredient-containing particles of the present invention are contained in place of the porous resin particles of the present invention.

Coating Material

The coating material of the present invention contains the porous resin particles. The coating material preferably contains a dispersion liquid mentioned earlier. In other words, the coating material preferably contains both the porous resin particles and the hydrophilic dispersion medium.

The coating material may contain a binder resin where necessary. The binder resin may be a resin soluble in a hydrophilic dispersion medium described above or an emulsion-type binder resin dispersible in a hydrophilic dispersion medium described above.

Examples of the binder resin include acrylic resins, alkyd resins, polyester resins, polyurethane resins, chlorinated polyolefin resins, and amorphous polyolefin resins. Any one of these binder resins may be selected as appropriate according to various conditions including the adhesion of the coating material to the base material to be coated and the environment in which the coating material is to be used.

The amount of the porous resin particles in the coating material may vary depending on, for example, the thickness of the coating film to be formed, the average particle diameter of the porous resin particles, and coating methods. The amount of the porous resin particles is preferably from 5 wt % to 50 wt %, more preferably from 10 wt % to 50 wt %, and even more preferably from 20 wt % to 40 wt %, as based on the sum of the binder resin (only the solid content if an emulsion-type resin is used) and the porous resin particles. If the porous resin particles are less than 5 wt %, the porous resin particles may not produce sufficient matting effects. On the other hand, if the porous resin particles are more than 50 wt %, the coating material may have too great viscosity for the porous resin particles to sufficiently disperse, which could cause improper appearance, such as microcracks, in the resultant coating film or a rough surface of the coating film.

The coating material may contain, where necessary, any publicly known coating surface adjuster, fluidity adjuster, ultraviolet absorber, optical stabilizer, curing catalyst, extender pigment, coloring pigment, metal pigment, mica powder pigment, dye, or organic solvent except for the hydrophilic dispersion media.

A coating film may be formed of the coating material by any publicly known method that is by no means limited in any particular manner. Examples of the method of forming a coating film using the coating material include spray coating, roll coating, and brush coating. The coating material may be diluted with a diluent to adjust its viscosity when necessary. Examples of the diluent include hydrocarbon-based solvents, such as toluene and xylene; ketone-based solvents, such as methyl ethyl ketones and methyl isobutyl ketones; ester-based solvents, such as ethyl acetate and butyl acetate; ether-based solvents, such as dioxane and ethylene glycol diethylether; water; and alcohol-based solvents. Any one of these diluents may be used alone; alternatively, two or more of them may be combined for use.

Light Diffusion Member

Of the aforementioned coating materials containing the porous resin particles, those which contain a binder resin and which are transparent, i.e., those which contain a transparent binder resin and which do not contain non-transparent materials, such as pigments and dyes, may be used as a light-diffusing coating material, such as a paper coating material or a light diffusion member coating material. When this is the case, the porous resin particles act as a light diffusing agent.

The light diffusion member of the present invention may be manufactured by coating a transparent base material as a base material with a light-diffusing coating material (light diffusion member coating material) to form a transparent coating film (light-diffusing coating).

Examples of the transparent base material include any material suitably selected from resin base materials containing resin, such as polyethylene terephthalates (PETs), polyesters, acrylic resins, polycarbonates, and polyamides and inorganic base materials, such as a transparent glass sheet. The thickness of the transparent base material is by no means limited in any particular manner, but preferably from 10 µm to 500 µm with ease in fabrication and handling taken into consideration. The light-diffusing coating may be formed by any publicly known method, such as reverse roll coating, gravure coating, dye coating, comma coating, and spray coating. The thickness of the light-diffusing coating is by no means limited in any particular manner, but preferably from 1 µm to 100 µm and more preferably from 3 µm to 30 µm with, for example, light diffusibility and film strength taken into consideration.

Alternatively, the light diffusion member of the present invention may be manufactured by molding a light-diffusing resin composition prepared by dispersing the porous resin particles of the present invention as a light diffusing agent in a transparent base resin (transparent resin).

Examples of the transparent base resin include acrylic resins, alkyl(meth)acrylate styrene copolymers, polycarbonates, polyesters, polyethylenes, polypropylenes, and polystyrenes. Any one of these transparent base resins may be used alone; alternatively, two or more of them may be combined for use.

The porous resin particles are added to the transparent base resin in an amount of preferably from 0.01 parts by weight to 40 parts by weight, and more preferably from 0.1 parts by weight to 10 parts by weight, per 100 parts by weight of the transparent base resin. If the porous resin particles are added in an amount of less than 0.01 parts by weight, the resultant light diffusion member may not exhibit sufficient light diffusibility. If the porous resin particles are added in an amount of more than 40 parts by weight, the resultant light diffusion member exhibits sufficient light diffusibility, possibly, at the cost of the optical transparency of the light diffusion member.

The method of manufacturing the light-diffusing resin composition is by no means limited in any particular manner. The light-diffusing resin composition may be manufactured by mixing the porous resin particles and the transparent base resin by a publicly known, conventional method, such as mechanical pulverization/crushing mixing. According to mechanical pulverization/crushing mixing, the light-diffusing resin composition may be manufactured by mixing and stirring the porous resin particles and the transparent base resin using a Henschel mixer, a V-type mixer, a Turbula mixer, a hybridizer, a rocking mixer, or like apparatus.

The light diffusion member of the present invention is obtainable by molding the light-diffusing resin composition. The light-diffusing resin composition in pellet form may be molded, for example, by injection molding, injection compression molding, or extrusion molding into a molded article (light diffusion member). Alternatively, the light-diffusing resin composition may be extrusion-molded into a sheet-like molded article which is then further molded, for example, by vacuum molding or compressed air molding into a final molded article (light diffusion member).

Liquid-Chromatography Separating Agent

The porous resin particles of the present invention may be used as a liquid-chromatography separating agent. Therefore, the liquid-chromatography separating agent of the present invention contains the porous resin particles.

The liquid-chromatography separating agent is suitable for use in liquid chromatography that uses an aqueous phase medium (as a mobile phase) to separate out hydrophilic substances, especially, protein. Especially, the porous resin particles in the liquid-chromatography separating agent preferably have a high degree of crosslinking (e.g., the polymer in the porous resin particles is a polymer of a monomer mixture that contains the polyfunctional vinyl-based monomer in an amount of from more than 70 wt % to 98 wt %) and a high pore volume (e.g., from 0.50 $cm^3/g$ to 1.50 $cm^3/g$) because such a liquid-chromatography separating agent exhibits high affinity with the aqueous phase medium.

The liquid-chromatography separating agent is placed in, for example, a glass or metal chromatography column, which may be used as a packed liquid-chromatography column in the separation of hydrophilic substances.

EXAMPLES

The following will specifically describe the present invention by way of examples and comparative examples. The present invention is however by no means limited to these examples. First, various measurement and evaluation methods used in the examples and comparative examples will be described: namely, a method of measuring the volume-average particle diameter of resin particles, a method of measuring the specific surface area of resin particles, a method of measuring the pore diameter and pore volume of resin particles, a method of measuring the water absorption value of resin particles, a method of measuring the oil absorption value of resin particles, a method of evaluating the hydrophilicity of resin particles, a method of evaluating the redispersibility of resin particles in ethanol, and a method of evaluating the redispersibility of resin particles in water.

Method of Measuring Volume-Average Particle Diameter of Resin Particles

The volume-average particle diameter of resin particles was measured using a Coulter Multisizer III (measuring instrument manufactured by Beckman Coulter, Inc.). The measurement was carried out using an aperture calibrated as instructed in the user's manual for Multisizer™ 3 issued by Beckman Coulter, Inc.

Suitable apertures were selected for measurement: for example, 50 µm for the measurement of resin particles with a predicted volume-average particle diameter of from 1 µm to 10 µm, both inclusive; 100 µm for the measurement of resin particles with a predicted volume-average particle diameter of from 10 µm, exclusive, to 30 µm, inclusive; 280 µm for the measurement of resin particles with a predicted volume-average particle diameter of from 30 µm, exclusive, to 90 µm, inclusive; and 400 µm for the measurement of resin particles with a predicted volume-average particle diameter of from 90 µm, exclusive, to 150 µm, inclusive. When the measured volume-average particle diameter differed from the predicted volume-average particle diameter, another measurement was carried out after changing the aperture size to a proper one.

When the 50-µm aperture was selected, the aperture current was set to −800, and the gain was set to 4. When the 100-µm aperture was selected, the aperture current was set to −1,600, and the gain was set to 2. When the 280- or 400-µm aperture was selected, the aperture current was set to −3,200, and the gain was set to 1.

Resin particles (0.1 g) were dispersed in 10 ml of a 0.1 wt % aqueous solution of a nonionic surfactant using a touch mixer ("TOUCHMIXER MT-31" manufactured by Yamato Scientific Co., Ltd.) and an ultrasonic cleaner ("ULTRA-SONIC CLEANER VS-150" manufactured by Velvo-Clear) to prepare dispersion liquids, which were used as measurement samples. A beaker was filled with ISOTON® II (measurement electrolyte solution manufactured by Beckman Coulter, Inc.) and placed in the measurement section of the Coulter Multisizer III. Next, the dispersion liquid was dispensed dropwise into the beaker while gently stirring. The densitometer reading on the screen of the main body of the Coulter Multisizer III was then adjusted to 5% to 10% before measurement was started. Over the course of the measurement, the contents of the beaker were stirred so gently that no bubbles would form in the contents. The measurement was terminated when the measurement was done on 100,000 particles.

The volume-average particle diameter is an arithmetic average for a volume-based particle size distribution of 100,000 particles.

The coefficient of variation (CV) of particle diameters of resin particles was calculated using the following equation.

Coefficient of Variation of Particle Diameters of Resin Particles=(Standard Deviation of Volume-based Particle Size Distribution of Resin Particles/Volume-average Particle Diameter of Resin Particles)×100

Method of Measuring Specific Surface Area of Resin Particles

The specific surface area of resin particles was measured by BET (nitrogen adsorption method) described in ISO 9277 $1^{st}$ Ed., JIS Z 8830:2001. BET nitrogen adsorption isotherms were drawn for target resin particles using an automatic specific surface area and porosimetry analyzer, Tristar 3000, manufactured by Shimadzu Corporation, and a specific surface area was calculated from nitrogen adsorption levels by the BET multi-point method. Note that the specific surface area was measured by a constant volume method using nitrogen as the adsorbate with the adsorbate cross-sectional area being 0.162 $nm^2$ after a pretreatment by hot gas purging. More specifically, the pretreatment was carried out by: nitrogen-purging resin particles for 20 minutes while heating a container containing the resin particles at 65° C.; cooling the container at room temperature; and vacuum-deaerating the contents while heating the container at 65° C. until the internal pressure of the container dropped to less than or equal to 0.05 mmHg.

Table 1 shows the measured specific surface areas of the resin particles of Examples 1 to 7 and Comparative Examples 1 to 3.

Method of Measuring Pore Diameters and Pore Volumes of Resin Particles

The pore diameter (average pore diameter) and pore volume of resin particles were determined by the BJH method. Nitrogen desorption isotherms were drawn for target resin particles using an automatic specific surface area and porosimetry analyzer, Tristar 3000, manufactured by Shimadzu Corporation, and a pore diameter (average pore diameter) and pore volume (integral pore volume) were calculated by the BJH method. Note that the nitrogen desorption isotherms were drawn by a constant volume method using nitrogen as the adsorbate with the adsorbate cross-sectional area being 0.162 $nm^2$.

Table 1 also shows the measured pore diameters and pore volumes of the resin particles of Examples 1 to 7 and Comparative Examples 1 to 3.

Table 1 also shows the evaluated porosity of the resin particles of Examples 1 to 7 and Comparative Examples 1 to 3.

Method of Measuring Water Absorption Value of Resin Particles

The water absorption value of resin particles was measured by a modified JIS K 5101-13-2 measuring method. Distilled water was used in place of boiled linseed oil, and a new criterion was used to determine an end point. Details of the measurement of water absorption values follow.

(A) Devices and Tools

Measurement plate: Flat and smooth glass plate larger than 300×400×5 mm

Palette knife (spatula): Steel or stainless steel blade with handle

Chemical balance (weighing scales): Capable of measuring down to order of 10 mg

Burette: 10 ml capacity as specified in JIS R 3505

(B) Reagent: Distilled Water (C) Measuring Method (1) Resin particles (1 gram) were placed at the center of a measurement plate. Distilled water was gradually dispensed, 4 or 5 droplets at a time, from a burette to the center of the resin particles. Every time droplets were dispensed, both the resin particles and the distilled water were thoroughly kneaded with a palette knife.

(2) The dropwise dispensation and kneading were repeated until the whole resin particles and distilled water formed a hard, putty-like lump. After that, one droplet of distilled water was dispensed at a time and kneaded. An end point was regarded as having been reached when the dispensation of a droplet of distilled water abruptly softened the paste (kneaded article of resin particles and distilled water) so that the paste started to flow.

(3) Determining Flow

The paste was determined to have flown if the dispensation of a droplet of distilled water abruptly softened the paste so that the paste moved when the measurement plate was erected upright. If the paste did not move on the vertically erected measurement plate, another droplet of distilled water was dispensed.

(4) The amount of distilled water consumed up to the end point, as indicated by the decrease in the amount of the liquid in the burette, was read off the burette.

(5) Each measurement was completed within 7 to 15 minutes. If the measurement lasted more than 15 minutes, the measurement was started all over again. Only those results from measurements that were completed within a specified time were accepted.

(D) Calculating Water Absorption Value

The water absorption value per 100 g of the sample was calculated using the following equation:

$$W=(V/m)\times 100$$

where W is a water absorption value (ml/100 g), m is the weight of resin particles (g), and V is the volume consumed distilled water (ml).

Table 1 also shows the measured water absorption values of the resin particles of Examples 1 to 7 and Comparative Examples 1 to 3.

Method of Measuring Oil Absorption Value of Resin Particles

The oil absorption value of resin particles was measured by a modified JIS K 5101-13-2 measuring method. Purified linseed oil was used in place of boiled linseed oil, and a new criterion was used to determine an end point. Details of the measurement of oil absorption values follow.

(A) Devices and Tools

Measurement plate: Flat and smooth glass plate larger than 300×400×5 mm

Palette knife (spatula): Steel or stainless steel blade with handle

Chemical balance (weighing scales): Capable of measuring down to order of 10 mg

Burette: 10 ml capacity as specified in JIS R 3505

(B) Reagent

Purified linseed oil: As specified in ISO 150 (JIS first grade manufactured by (Wako Pure Chemical Industries Ltd.)

(C) Measuring Method (1) Resin particles (1 gram) were placed at the center of a measurement plate. Purified linseed oil was gradually dispensed, 4 or 5 droplets at a time, from a burette to the center of the resin particles. Every time droplets were dispensed, both the resin particles and the purified linseed oil were thoroughly kneaded with a palette knife.

(2) The dropwise dispensation and kneading were repeated until the whole resin particles and purified linseed oil formed a hard, putty-like lump. After that, one droplet of purified linseed oil was dispensed at a time and kneaded. An end point was regarded as having been reached when the dispensation of a droplet of purified linseed oil abruptly softened the paste (kneaded article of resin particles and purified linseed oil) so that the paste started to flow.

(3) Determining Flow

The paste was determined to have flown if the dispensation of a droplet of purified linseed oil abruptly softened the paste so that the paste moved when the measurement plate was erected upright. If the paste did not move on the vertically erected measurement plate, another droplet of purified linseed oil was dispensed.

(4) The amount of purified linseed oil consumed up to the end point, as indicated by the decrease in the amount of the liquid in the burette, was read off the burette.

(5) Each measurement was completed within 7 to 15 minutes. If the measurement lasted more than 15 minutes, the measurement was started all over again. Only those results from measurements that were completed within a specified time were accepted.

(D) Calculating Oil Absorption Value

The oil absorption value per 100 g of the sample was calculated using the following equation:

$$O=(V/m)\times 100$$

where O is an oil absorption value (ml/100 g), m is the weight of resin particles (g), and V is the volume of consumed purified linseed oil (ml).

Table 1 also shows the measured oil absorption values of the resin particles of Examples 1 to 7 and Comparative Examples 1 to 3.

Evaluating Hydrophilicity of Resin Particles

After placing 100 ml of distilled water in a glass beaker (capacity: 100 ml), 0.2 g of resin particles were floated on the water surface, and the top of the glass beaker was sealed with plastic wrap. Thereafter, the glass beaker was let to stand to observe precipitation of the resin particles. The time that the resin particles took to precipitate was measured. In this evaluation of hydrophilicity, the resin particles were rated very hydrophilic (indicated by "VH" in Table 1) if they precipitated completely in less than 2 hours after they were let to stand, sufficiently hydrophilic (indicated by "S" in Table 1) if they precipitated completely in 2 hours to less than 12 hours after they were let to stand, poorly hydrophilic (indicated by "PH" in Table 1) if they precipitated completely in 12 hours to less than 24 hours after they were let to stand, and very poorly hydrophilic (indicated by "VPH" in Table 1) if no particles precipitated at all in 24 hours after they were let to stand.

Table 1 also shows the evaluated hydrophilicity of the resin particles of Examples 1 to 7 and Comparative Examples 1 to 3.

Evaluating Redispersibility of Resin Particles in Ethanol

Resin particles (0.5 g) were weighed out in a graduated test tube manufactured by Maruemu Corporation (product name: "Screw Capped Test Tube NR-10"). After 10 ml of commercially available special-grade ethanol (99.5 vol % or higher purity) was added to the weighed-out resin particles, the resin particles were dispersed in the ethanol using a touch mixer (mag-mixer of touch drive-type) until the resin particles were completely dispersed in the ethanol. The dispersion liquid hence became entirely clouded (the dispersion liquid had a volume of about 10 ml).

Next, the test tube was let to stand for 12 hours to precipitate the resin particles. Then, the test tube was shaken by hand to redisperse the resin particles in the ethanol. The number of times the test tube needed to be shaken to redisperse the resin particles in the ethanol was recorded to evaluate how easily the resin particles redispersed.

In the evaluation of the redispersibility of the resin particles of the examples and comparative examples of the invention in ethanol, the test tube was shaken by hand to produce a uniform mixture. The number of shakes needed to uniformly disperse all the precipitated resin particles in ethanol was used as an indicator in the evaluation of the redispersibility of resin particles. Swinging the test tube reciprocally once with an amplitude of about 10 cm was counted as one complete shake. The dispersion of the resin particles was visually checked for each shake to determine the number of shakes needed to uniformly disperse all the precipitated resin particles.

In the evaluation of redispersibility in ethanol, the resin particles were rated acceptable (indicated by "A" in Table 1) if they took 60 or fewer shakes to be thoroughly and uniformly dispersed and non-acceptable (indicated by "NA" in Table 1) if they took more than 60 shakes to be thoroughly and uniformly dispersed.

Table 1 also shows the evaluated redispersibility of the resin particles of Examples 1 to 7 and Comparative Examples 1 to 3 in ethanol.

Evaluating Redispersibility of Resin Particles in Water

Resin particles (0.5 g) were weighed out in a graduated test tube manufactured by Maruemu Corporation (product name: "Screw Capped Test Tube NR-10"). After 10 ml of distilled water was added to the weighed-out resin particles, the resin particles were dispersed in the water by repeatedly mixing in a touch mixer (mag-mixer of touch drive-type) and applying ultrasonic waves using an ultrasonic cleaner manufactured by Velvo-Clear ("ULTRASONIC CLEANER VS-150") until the resin particles were completely dispersed in the water. The dispersion liquid hence became entirely clouded (the dispersion liquid had a volume of about 10 ml).

Next, the test tube was let to stand for 12 hours to precipitate the resin particles. Then, the test tube was shaken by hand to redisperse the resin particles in the water. The number of times the test tube needed to be shaken to redisperse the resin particles in the water was recorded to evaluate how easily the resin particles redispersed.

In the evaluation of the redispersibility of the resin particles of the examples and comparative examples of the invention in water, the test tube was shaken by hand to produce a uniform mixture. The number of shakes needed to uniformly disperse all the precipitated resin particles in water was used as an indicator in the evaluation of the redispersibility of the resin particles. Swinging the test tube reciprocally once with an amplitude of about 10 cm was counted as one complete shake. The dispersion of the resin particles was visually checked for each shake to determine the number of shakes needed to uniformly disperse all the precipitated resin particles.

In the evaluation of redispersibility in water, the resin particles were rated acceptable (indicated by "A" in Table 1) if they took 80 or fewer shakes to be thoroughly and uniformly dispersed and non-acceptable (indicated by "NA" in Table 1) if they took more than 80 shakes to be thoroughly and uniformly dispersed.

Table 1 also shows the evaluated redispersibility of the resin particles of Examples 1 to 7 and Comparative Examples 1 to 3 in water.

Example 1

A 5-L autoclave equipped with a stirrer and a thermometer was charged with an aqueous solution in which sodium lauryl sulfate (0.30 g, or 0.01 parts by weight per 100 parts by weight of water) as an anionic surfactant and 35% betaine lauryl dimethylamino acetate (1.71 g, or an equivalent of 0.02 parts by weight of pure betaine lauryl dimethylamino acetate per 100 parts by weight of water) as a zwitterionic surfactant were dissolved in 3,000 g of water (aqueous medium). Then, magnesium pyrophosphate (60 g) prepared by double decomposition as a dispersion stabilizer was dispersed in the aqueous solution in the autoclave to obtain a dispersion liquid (aqueous phase).

Methyl methacrylate (MMA) (12.5 g, 5 wt % as based on the total monomers) as another monofunctional vinyl-based monomer, 12.5 g (5 wt % as based on the total monomers) of a poly(ethylene glycol-propylene glycol) monomethacrylate (trade name: "Blemmer® 50 PEP-300," manufactured by NOF Corporation, a mixture of compounds of general formula (1) where R is $CH_3$, 1 is about 3.5 on average, and m is about 2.5 on average) as a mono(meth)acrylate-based monomer, 225 g (90 wt % as based on the total monomers) of ethylene glycol dimethacrylate (EGDMA) as a polyfunctional vinyl-based monomer, 750 g (300 parts by weight per 100 parts by weight of the total monomers) of ethyl acetate as a pore-forming agent, and 0.75 g of 2,2'-azobis(2,4-dimethylvaleronitrile) as a polymerization initiator were mixed and dissolved to prepare a monomer mixture solution.

The monomer mixture solution prepared in advance was poured into the dispersion liquid (aqueous phase) in the autoclave. The contents of the autoclave were stirred with a high-speed emulsifier/disperser (trade name: "T.K. Homo-mixer," manufactured by Primix Corporation) at a rotational speed of 6000 rpm for 5 minutes, to prepare a suspension of the monomer mixture solution with a droplet diameter of approximately 8 μm. Next, the internal temperature of the autoclave was raised to 50° C. to start suspension-polymerizing the monomer mixture solution while stirring the contents of the autoclave. The monomer mixture solution was continuously heated at 70° C. for 2 hours to undergo suspension polymerization, to obtain a slurry.

Thereafter, while maintaining the jacket of the autoclave at 70° C., the internal pressure was reduced to −500 mmHg to remove ethyl acetate from the slurry. The slurry in the autoclave was then cooled down. Hydrochloric acid was added until the slurry showed a pH of 2 or less to decompose the magnesium pyrophosphate. The slurry was washed in water and dehydrated in a centrifugal dehydrator to obtain a cake. The cake was dried in a vacuum in a vacuum drier at 80° C. and run through a sieve with 45 μm openings, to obtain target resin particles.

The obtained resin particles had an average particle diameter of 5.4 μm.

The obtained resin particles were imaged under a scanning electron microscope (SEM). They turned out to be spherical and porous with multiple pores as shown in the SEM image in FIG. 1.

Example 2

Resin particles were obtained by following the same procedures as in Example 1, except that: no methyl methacrylate (MMA) was used as another monofunctional vinyl-based monomer; and the amount of ethylene glycol dimethacrylate (EGDMA) used as a polyfunctional vinyl-based monomer was changed to 237.5 g (95 wt % as based on the total monomers).

The obtained resin particles had a volume-average particle diameter of 7.8 μm.

The obtained resin particles were imaged under a scanning electron microscope (SEM). They turned out to be spherical and porous with multiple pores like the resin particles of Example 1 (see FIG. 1).

Example 3

Resin particles were obtained by following the same procedures as in Example 1, except that: the amount of methyl methacrylate (MMA) used as another monofunctional vinyl-based monomer was changed to 50 g (20 wt % as based on the total monomers); and the amount of ethylene glycol dimethacrylate (EGDMA) used as a polyfunctional vinyl-based monomer was changed to 187.5 g (75 wt % as based on the total monomers).

The obtained resin particles had a volume-average particle diameter of 8.6 μm.

The obtained resin particles were imaged under a scanning electron microscope (SEM). They turned out to be spherical and porous with multiple pores like the resin particles of Example 1 (see FIG. 1).

Example 4

Resin particles were obtained by following the same procedures as in Example 1, except that: 12.5 g (5 wt % as based on the total monomers) of lactone-modified hydroxyethyl methacrylate (trade name: "Placcel® FM3," manufactured by Daicel Corporation, a compound of general formula (2) where R is $CH_3$, and p is 3) was used, as a mono(meth)acrylate-based monomer, in place of 12.5 g (5 wt % as based on the total monomers) of a poly(ethylene glycol-propylene glycol) monomethacrylate (trade name: "Blemmer® 50 PEP-300," manufactured by NOF Corporation, a mixture of compounds of general formula (1) where R is $CH_3$, 1 is about 3.5 on average, and m is about 2.5 on average).

The obtained resin particles had a volume-average particle diameter of 8.5 μm.

The obtained resin particles were imaged under a scanning electron microscope (SEM). They turned out to be spherical and porous with multiple pores like the resin particles of Example 1 (see FIG. 1).

Example 5

Resin particles were obtained by following the same procedures as in Example 1, except that: no methyl methacrylate (MMA) was used as another monofunctional vinyl-based monomer; the amount of poly(ethylene glycol-propylene glycol) monomethacrylate (trade name: "Blemmer® 50 PEP-300," manufactured by NOF Corporation, a mixture of compounds of general formula (1) where R is $CH_3$, l is about 3.5 on average, and m is about 2.5 on average) used as a mono(meth)acrylate-based monomer was changed to 50 g (20 wt % as based on the total monomers); and the amount of ethylene glycol dimethacrylate (EGDMA) used as a polyfunctional vinyl-based monomer was changed to 200 g (80 wt % as based on the total monomers).

The obtained resin particles had a volume-average particle diameter of 7.7 μm.

The obtained resin particles were imaged under a scanning electron microscope (SEM). They turned out to be spherical and porous with multiple pores like the resin particles of Example 1 (see FIG. 1).

Example 6

Resin particles were obtained by following the same procedures as in Example 1, except that: 12.5 g (5 wt % as based on the total monomers) of ethyl methacrylate (EMA) was used, as another monofunctional vinyl-based monomer, in place of 12.5 g (5 wt % as based on the total monomers) of methyl methacrylate (MMA).

The obtained resin particles had a volume-average particle diameter of 7.6 μm.

The obtained resin particles were imaged under a scanning electron microscope (SEM). They turned out to be spherical and porous with multiple pores like the resin particles of Example 1 (see FIG. 1).

Example 7

Resin particles were obtained by following the same procedures as in Example 1, except that: the amount of poly(ethylene glycol-propylene glycol) monomethacrylate (trade name: "Blemmer® 50 PEP-300," manufactured by NOF Corporation, a mixture of compounds of general formula (1) where R is $CH_3$, l is about 3.5 on average, and m is about 2.5 on average) used as a mono(meth)acrylate-based monomer was changed to 25.0 g (10 wt % as based on the total monomers); the amount of ethylene glycol dimethacrylate (EGDMA) used as a polyfunctional vinyl-based monomer was changed to 200 g (80 wt % as based on the total monomers); and 12.5 g (5 wt % as based on the total monomers) of trimethylolpropane trimethacrylate (TMP) was added as another polyfunctional vinyl-based monomer in the preparation of the monomer mixture solution.

The obtained resin particles had a volume-average particle diameter of 7.2 μm.

The obtained resin particles were imaged under a scanning electron microscope (SEM). They turned out to be spherical and porous with multiple pores like the resin particles of Example 1 (see FIG. 1).

Comparative Example 1

Resin particles were obtained by following the same procedures as in Example 1, except that: the amount of sodium lauryl sulfate used as an anionic surfactant was changed to 0.24 g (0.01 parts by weight per 100 parts by weight of water); the amount of 35% betaine lauryl dimethylamino acetate used as a zwitterionic surfactant was changed to 1.37 g (equivalent of 0.02 parts by weight of pure betaine lauryl dimethylamino acetate per 100 parts by weight of water); the amount of water (aqueous medium) used was changed to 2,400 g; the amount of magnesium pyrophosphate used was changed to 48 g; no poly(ethylene glycol-propylene glycol) monomethacrylate (trade name: "Blemmer® 50 PEP-300," manufactured by NOF Corporation, a mixture of compounds of general formula (1) where R is $CH_3$, l is about 3.5 on average, and m is about 2.5 on average) was used as a mono(meth)acrylate-based monomer; the amount of methyl methacrylate (MMA) used as another monofunctional vinyl-based monomer was changed to 360 g (60 wt % as based on the total monomers); the amount of ethylene glycol dimethacrylate (EGDMA) used as a polyfunctional vinyl-based monomer was changed to 240 g (40 wt % as based on the total monomers); the amount of ethyl acetate used as a pore-forming agent was changed to 600 g (100 parts by weight per 100 parts by weight of the total monomers); the amount of 2,2'-azobis(2,4-dimethylvaleronitrile) used as a polymerization initiator was changed to 1.8 g; and the duration of stirring at a rotational speed of 6000 rpm in the high speed emulsifier/disperser (trade name: "T.K. Homomixer," manufactured by Primix Corporation) was changed to 10 minutes.

The obtained resin particles had a volume-average particle diameter of 8.3 μm.

Figure 2:
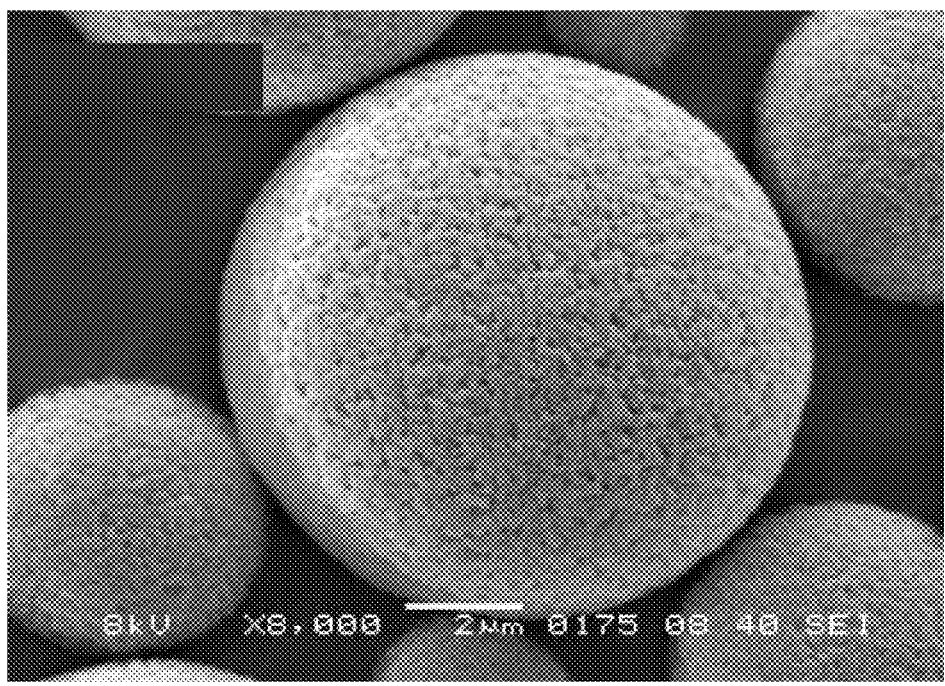
FIG. 2 is a scanning electron microscope (SEM) image of porous resin particles in accordance with Comparative Example 1.

The obtained resin particles were imaged under a scanning electron microscope (SEM). They turned out to be spherical and porous with multiple pores as shown in the SEM image in FIG. 2.

Comparative Example 2

Resin particles were obtained by following the same procedures as in Example 1, except that: the amount of sodium lauryl sulfate used as an anionic surfactant was changed to 0.24 g (0.01 parts by weight per 100 parts by weight of water); the amount of 35% betaine lauryl dimethylamino acetate used as a zwitterionic surfactant was changed to 1.37 g (equivalent of 0.02 parts by weight of pure betaine lauryl dimethylamino acetate per 100 parts by weight of water); the amount of water (aqueous medium) used was changed to 2,400 g; the amount of magnesium pyrophosphate used was changed to 48 g; the amount of methyl methacrylate (MMA) used as another monofunctional vinyl-based monomer was changed to 354 g (59 wt % as based on the total monomers); the amount of poly (ethylene glycol-propylene glycol) monomethacrylate (trade name: "Blemmer® 50 PEP-300," manufactured by NOF Corporation, a mixture of compounds of general formula (1) where R is $CH_3$, l is about 3.5 on average, and m is about 2.5 on average) used as a mono(meth)acrylate-based monomer was changed to 6 g (1 wt % as based on the total monomers); the amount of ethylene glycol dimethacrylate (EGDMA) used as a polyfunctional vinyl-based monomer was changed to 240 g (40 wt % as based on the total monomers); the amount of ethyl acetate used as a pore-forming agent was changed to 600 g (100 parts by weight per 100 parts by weight of the total monomers); the amount of 2,2'-azobis(2,4-dimethylvaleronitrile) used as a polymerization initiator was changed to 1.8 g; and the duration of stirring at a rotational speed of 6000 rpm in the high speed emulsifier/disperser (trade name: "T.K. Homomixer," manufactured by Primix Corporation) was changed to 10 minutes.

The obtained resin particles had a volume-average particle diameter of 7.9 μm.

Figure 3:
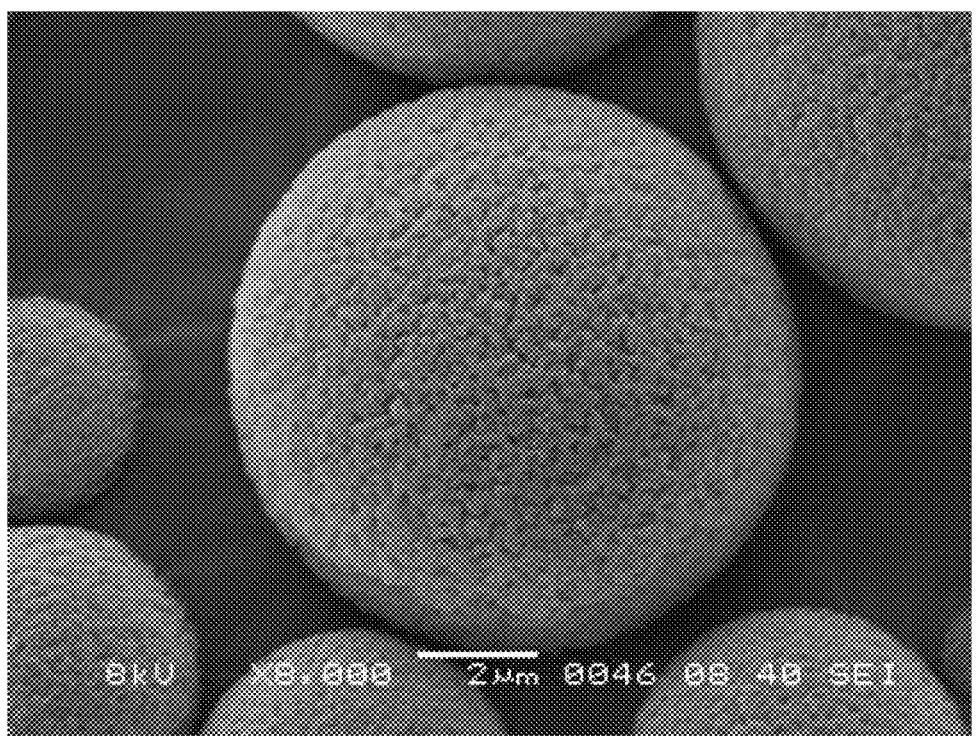
FIG. 3 is a scanning electron microscope (SEM) image of porous resin particles in accordance with Comparative Example 2.

The obtained resin particles were imaged under a scanning electron microscope (SEM). They turned out to be spherical and porous with multiple pores as shown in the SEM image in FIG. 3.

Comparative Example 3

Resin particles were obtained by following the same procedures as in Example 1, except that: no sodium lauryl sulfate, no 35% betaine lauryl dimethylamino acetate, and no ethyl acetate were used; the amount of water (aqueous medium) used was changed to 2,400 g; the amount of magnesium pyrophosphate used was changed to 48 g; the amount of methyl methacrylate (MMA) used as another monofunctional vinyl-based monomer was changed to 960 g (80 wt % as based on the total monomers); the amount of poly(ethylene glycol-propylene glycol) monomethacrylate (trade name: "Blemmer® 50 PEP-300," manufactured by NOF Corporation, a mixture of compounds of general formula (1) where R is $CH_3$, l is about 3.5 on average, and m is about 2.5 on average) used as a mono(meth)acrylate-based monomer was changed to 180 g (15 wt % as based on the total monomers); the amount of ethylene glycol dimethacrylate (EGDMA) used as a polyfunctional vinyl-based monomer was changed to 60 g (5 wt % as based on the total monomers); the amount of 2,2'-azobis(2,4-dimethylvaleronitrile) used as a polymerization initiator was changed to 1.8 g; and the duration of stirring at a rotational speed of 6000 rpm in the high speed emulsifier/disperser (trade name: "T.K. Homomixer," manufactured by Primix Corporation) was changed to 10 minutes.

The obtained resin particles had a volume-average particle diameter of 7.2 μm.

Figure 4:
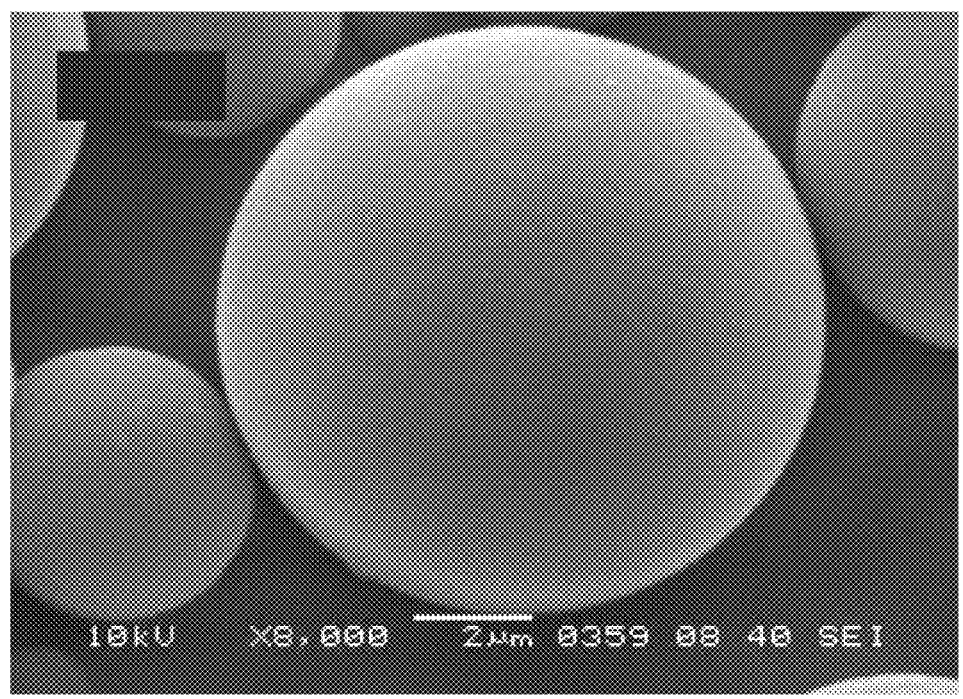
FIG. 4 is a scanning electron microscope (SEM) image of porous resin particles in accordance with Comparative Example 3.

The obtained resin particles were imaged under a scanning electron microscope (SEM). They turned out to be spherical, but not porous, as shown in the SEM image in FIG. 4.

Table 1 also shows the monomer composition and the amount (in parts by weight) of pore-forming agent used per 100 parts by weight of total monomers for the resin particles of Examples 1 to 7 and Comparative Examples 1 to 3. Table 1 further shows the measured volume-average particle diameter, measured specific surface area, measured pore diameter, measured pore volume, measured oil absorption value, measured water absorption value, evaluated hydrophilicity, evaluated redispersibility in ethanol, and evaluated redispersibility in water of the resin particles of Examples 1 to 7 and Comparative Examples 1 to 3. The resin particles of Comparative Example 1 did not disperse in distilled water in the evaluation of their hydrophilicity. The water absorption value of the resin particles of Comparative Example 1 could not be measured because distilled water did not infiltrate into them. The redispersibility in water of the resin particles of Comparative Example 1 could not be evaluated because the resin particles did not disperse in distilled water. The pore diameter and pore volume of the resin particles of Comparative Example 3 were not measured because they had very small specific surface areas and were not porous.

TABLE 1

| | | | Ex. 1 | Ex. 2 | Ex. 3 | Ex. 4 | Ex. 5 | Ex. 6 | Ex. 7 | Comp. Ex. 1 | Comp. Ex. 2 | Comp. Ex. 3 |
|---|---|---|---|---|---|---|---|---|---|---|---|---|
| Monomer Composition | Other Monofunctional Monomer | MMA (wt %) | 5 | — | 20 | 5 | — | — | 5 | 60 | 59 | 80 |
| | | EMA (wt %) | — | — | — | — | — | 5 | — | — | — | — |
| | Mono(meth)acrylate-based Monomer | Blemmer ®50 PEP-300 (wt %) | 5 | 5 | 5 | — | 20 | 5 | 10 | — | 1 | 15 |
| | | Placcel ® FM3 (wt %) | — | — | — | 5 | — | — | — | — | — | — |
| | Polyfunctional Vinyl-based Monomer | EGDMA (wt %) | 90 | 95 | 75 | 90 | 80 | 90 | 80 | 40 | 40 | 5 |
| | | TMP (wt %) | — | — | — | — | — | — | 5 | — | — | — |
| Pore-forming Agent | Ethyl Acetate (parts by weight per 100 parts by weight of Monomer) | | 300 | 300 | 300 | 300 | 300 | 300 | 300 | 100 | 100 | — |
| Vol.-average Particle Diameter (μm) | | | 5.4 | 7.8 | 8.6 | 8.5 | 7.7 | 7.6 | 7.2 | 8.3 | 7.9 | 7.2 |
| SSA ($m^2/g$) | | | 347 | 305 | 418 | 323 | 224 | 380 | 320 | 85.2 | 78.8 | 0.7 |
| Pore Diam. (nm) | | | 9.7 | 10.0 | 11.1 | 10.5 | 11.5 | 9.3 | 8.6 | 11.3 | 12.6 | — |
| Pore Vol. ($cm^3/g$) | | | 0.84 | 0.76 | 1.16 | 0.78 | 0.65 | 0.89 | 0.68 | 0.30 | 0.24 | — |
| Oil AV (ml/100 g) | | | 515 | 485 | 476 | 498 | 465 | 535 | 539 | 142 | 140 | 75 |
| Water AV (ml/100 g) | | | 501 | 534 | 405 | 475 | 457 | 511 | 505 | — | 125 | 112 |
| Hydrophilicity | Time to Precipitate (min.) | | 20 | 30 | 40 | 20 | 20 | 20 | 20 | * | 720 | 90 |
| | Evaluation | | VH | VH | VH | VH | VH | VH | VH | VPH | PH | VH |
| Redispersibility in Ethanol | Number of Shakes | | 1 | 1 | 1 | 1 | 1 | 1 | 1 | 24 | 20 | 130 |
| | Evaluation | | A | A | A | A | A | A | A | A | A | NA |
| Redispersibility in Water | Number of Shakes | | 1 | 1 | 1 | 1 | 1 | 1 | 1 | — | 120 | 25 |
| | Evaluation | | A | A | A | A | A | A | A | — | NA | A |

* No precipitation even after 48 hours.

Ex.: "Example," Comp. Ex.: "Comparative Example," SSA: "Specific Surface Area," Diam.: "Diameter," Vol.: "Volume," AV: "Absorption Value," VH: "Very Hydrophilic," S: "Sufficiently Hydrophilic," PH: "Poorly Hydrophilic," VPH: "Very Poorly Hydrophilic," A: "Acceptable," NA: "Not acceptable."

As could be understood from the results shown in Table 1, the resin particles of Examples 1 to 7 are porous (namely, porous resin particles) and excellent in all of water absorbance, oil absorbance, hydrophilicity, redispersibility in ethanol, and redispersibility in water.

Specifically, the resin particles of Examples 1 to 7 have water absorption values of more than 400 ml per 100 g (more specifically, from 405 ml per 100 g to 534 ml per 100 g), which are far higher than the water absorption values of the resin particles of Comparative Examples 2 and 3 (112 ml per 100 g to 125 ml per 100 g). The resin particles of Examples 1 to 7 also have oil absorption values of more than 400 ml per 100 g (more specifically, from 465 ml per 100 g to 539 ml per 100 g), which are far higher than the oil absorption values of the resin particles of Comparative Examples 1 to 3 (75 ml per 100 g to 142 ml per 100 g).

The resin particles of Examples 1 to 7, which were obtained by polymerization of a monomer mixture containing 2 wt % to less than 30 wt % (specifically, 5 wt % to 20 wt %) mono(meth)acrylate-based monomer and more than 70 wt % to 98 wt % (specifically, 75 wt % to 95 wt %) polyfunctional vinyl-based monomer, are far better in water absorbance and oil absorbance than the resin particles of Comparative Examples 1 to 3, which were obtained from a monomer mixture containing less than 70 wt % polyfunctional vinyl-based monomer.

The resin particles of Examples 1 to 7, which were obtained by polymerization of a monomer mixture containing 2 wt % to less than 30 wt % (specifically, 5 wt % to 20 wt %) mono(meth)acrylate-based monomer and more than 70 wt % to 98 wt % (specifically, 75 wt % to 95 wt %) polyfunctional vinyl-based monomer, are more hydrophilic than the resin particles of Comparative Examples 1 and 2, which were obtained by polymerization of a monomer mixture containing less than 2 wt % mono(meth)acrylate-based monomer.

After measuring the water absorption values of the resin particles of Examples 1 to 7, the resin particles having absorbed water were dried to vaporize its water content and observed using a magnifying projector. They turned out to have preserved the spherical shape like the one in FIG. 1. If the resin particles of Examples 1 to 7, being spherical and porous as evidenced here, are blended into a cosmetic material or like external preparation, they provide improved spreadability and slippage in applying the external preparation to the skin. The resin particles of Examples 1 to 7 also scatter light in various directions on the skin surface to which the external preparation is applied, which conceals spots, freckles, and pores. Since the resin particles of Examples 1 to 7 are spherical and porous, if they are blended in a coating material, they improve the slippage of the coating material when applied to the base material. The resin particles also scatter the light that travels through the coating film formed on the base material and reflects off the base material. Furthermore, since the resin particles of Examples 1 to 7 are spherical and porous, if they are blended in a light diffusion member, they scatter light that reflects off the light diffusion member.

Example 8: Example of Body Lotion Manufacture

The resin particles (porous resin particles) obtained in Example 1 (3 parts by weight), ethanol (50 parts by weight) as a dispersion medium, glycyrrhizic acid (0.1 parts by weight) as an anti-inflammatory agent, purified water (46.4 parts by weight) as other dispersion media, and a fragrance (0.5 parts by weight) were mixed thoroughly in a mixer to obtain a body lotion as an external preparation.

The obtained body lotion provided very good slippage when applied to the skin, was smooth, and gave an excellent feel when used. The precipitated resin particles were readily redispersed by merely shaking the body lotion lightly before use, which made the body lotion easy to use. Furthermore, the body lotion was so good in water absorbance and oil absorbance that it could absorb sweat and sebum and keep the skin smooth and silky when applied to the skin.

Example 9: Example of Pre-Shave Lotion Manufacturing

The resin particles (porous resin particles) obtained in Example 1 (4 parts by weight), ethanol (91 parts by weight) as a dispersion medium, 1,3-butylene glycol (5.0 parts by weight) and cetyl ethylhexanoate (2.0 parts by weight) as other dispersion media, and a fragrance (suitable amount) were mixed thoroughly in a mixer to obtain a pre-shave lotion as an external preparation.

The obtained pre-shave lotion provided very good slippage when applied to the skin, was smooth, and gave an excellent feel when used. The precipitated resin particles were readily redispersed by merely shaking the pre-shave lotion lightly before use, which made the pre-shave lotion easy to use. Furthermore, the pre-shave lotion was so good in water absorbance and oil absorbance that it could absorb sweat and sebum and keep the skin smooth and silky when applied to the skin.

Example 10: Example of Powder Foundation Manufacturing

The resin particles (porous resin particles) obtained in Example 1 (15 parts by weight), sericite (21 parts by weight) as a clay mineral, white mica (51 parts by weight) as another clay mineral, red iron oxide (0.6 parts by weight) as a color ingredient, yellow iron oxide (1 part by weight) as another color ingredient, and a black iron oxide (0.1 parts by weight) as yet another color ingredient were mixed in a Henschel mixer to obtain a mixture. Next, to this mixture was added a mixture prepared by mixing and dissolving 10 parts by weight of cetyl 2-ethylhexanoate, 1 part by weight of sorbitan sesquioleate, and 0.2 parts by weight of a preservative. The entire mixture was uniformly mixed. A fragrance (0.1 parts by weight) was further added to the obtained mixture and mixed. After that, the mixture was pulverized and sieved. The pulverized and sieved article was compression-molded on a metal plate to obtain powder foundation.

The obtained powder foundation provided very good slippage when applied to the skin, was smooth, and gave an excellent feel when used. The powder foundation was so good in water absorbance and oil absorbance that it could absorb sweat and sebum and keep the skin smooth and silky when applied to the skin. The powder foundation also fixed skin flaws (concealed spots, freckles, pores, etc.) when applied to the skin.

Example 11: Example of Emulsion Foundation Manufacturing

The resin particles (porous resin particles) obtained in Example 1 (20.0 parts by weight), sericite (6.0 parts by weight) as a clay mineral, titanium dioxide (3.0 parts by weight), and a pigment (suitable amount) were mixed in a kneader to prepare a powder ingredient.

Separately from the powder ingredient, 5.0 parts by weight of polyethylene glycol (polyethylene glycol 4000), 1.0 part by weight of triethanolamine as a pH-adjuster, 5.0 parts by weight of propylene glycol, and 0.5 parts by weight of Veegum®, manufactured by Vanderbilt, as a clay mineral were added to 50.2 parts by weight of purified water and heated so that they could dissolve. To this obtained solution was added the previously prepared powder ingredient. After the powder was uniformly dispersed in a Homomixer, the mixture was maintained at 70° C. to obtain an aqueous phase component.

Next, separately from the aqueous phase component, 2.0 parts by weight of stearic acid, 0.3 parts by weight of cetyl alcohol, 20.0 parts by weight of liquid paraffin, a fragrance (suitable amount), and a preservative (suitable amount) were mixed and heated so that they could dissolve. After that, the mixture was maintained at 70° C. to obtain an oil phase component.

The aqueous phase component was added to the oil phase component. The mixture was subjected to preliminary emulsification, and uniformly emulsified and dispersed in a Homomixer. After that, the mixture was cooled down while stirring, to obtain emulsion foundation.

The obtained emulsion foundation provided very good slippage when applied to the skin, was smooth, and gave an excellent feel when used. The powder foundation was so good in water absorbance and oil absorbance that it could absorb sweat and sebum and keep the skin smooth and silky when applied to the skin. The emulsion foundation fixed skin flaws (concealed spots, freckles, pores, etc.) when applied to the skin.

Example 12: Example of Loose Powder Manufacturing

The resin particles (porous resin particles) obtained in Example 1 (21.0 parts by weight), mica (30.0 parts by weight) as a clay mineral, sericite (30.0 parts by weight) as another clay mineral, titanium sericite (9.0 parts by weight) as yet another clay mineral, titanium dioxide (8.0 parts by weight), and iron oxide (2.0 parts by weight) as a color ingredient were mixed in a Henschel mixer. After that, the mixture was pulverized once with a rotor speed mill, ZM-100, manufactured by Retsch (a 12-blade rotor was used with a 1-mm screen being attached and at a rotational speed of 14,000 rpm) to obtain loose powder.

The obtained loose powder provided very good slippage when applied to the skin, was smooth, and gave an excellent feel when used. The loose powder, when applied to the skin, so quickly absorbs sweat and sebum that it could provide excellent durability to makeup. The loose powder also fixed skin flaws (concealed spots, freckles, pores, etc.).

Example 13: Example of Body Powder Manufacturing

The resin particles (porous resin particles) obtained in Example (50.0 parts by weight), mica (25.0 parts by weight) as a clay mineral, and sericite (25.0 parts by weight) as another clay mineral were mixed in a Henschel mixer. After that, the mixture was pulverized once with a rotor speed mill, ZM-100, manufactured by Retsch (a 12-blade rotor was used with a 1-mm screen being attached and at a rotational speed of 14,000 rpm) to obtain body powder.

The obtained body powder provided very good slippage when applied to the skin, gave an excellent feel when used, and quickly absorbed sweat and sebum.

Example 14: Example of Coating Material Manufacturing

The resin particles (porous resin particles) obtained in Example 1 (3 parts by weight) and a commercially available aqueous solution of resin binder (containing 30% solid content, manufactured by Alberdingk, trade name "U330") (20 parts by weight) were stirred for 3 minutes using a centrifugal stirrer to obtain a dispersion liquid. In this process, the resin particles were readily dispersed in the aqueous resin binder by stirring for 3 minutes using a centrifugal stirrer.

The obtained dispersion liquid was left to stand for 3 hours. After that, the dispersion liquid was stirred again for 3 minutes using the centrifugal stirrer to obtain a coating material.

The obtained coating material exhibited such good redispersibility that the resin particles could be redispersed by merely shaking it even after 12 hours.

Coating of Acrylic Board

A 3-mm thick acrylic board was spray-coated with the coating material to prepare a 50-μm thick matting coating film. The obtained coating film did not have any visible bumps (projections) and exhibited good matting properties.

Example 15: Example of Light Diffusion Member Manufacturing

A 1:1 toluene/methyl ethyl ketone mixed solution (6 parts by weight) was added to a dispersion liquid containing a mixture of 3 parts by weight of the resin particles (porous resin particles) obtained in Example 1 and 4.5 parts by weight of an acrylic-based binder manufactured by Mitsubishi Rayon Co., Ltd. (trade name: "Dianal® LR-102"). The resultant mixture was stirred for 3 minutes in a centrifugal stirrer. The obtained solution was left to stand for 3 hours. After that, it was stirred again for 3 minutes in the centrifugal stirrer. Next, the obtained solution was applied onto a PET film using a 100-μm coater. A coating film was formed on the PET film by drying the obtained film for 1 hour in a drier that was maintained at 70° C., to obtain a light diffusion film as a light diffusion member.

The face to be coated of the obtained light diffusion film was polished with a cloth reciprocally 20 times using a fastness rubbing tester and after the polishing, visually inspected for scratches on the light diffusion film. No line scratches or resin particle peelings were observed, which confirmed that the resin particles were compatible with the acrylic-based binder in the coating film. The obtained light diffusion film also exhibited good light diffusibility because of the blended resin particles.

Example 16: Example of Medicinal-Ingredient-Containing Particle Manufacturing The resin particles (porous resin particles) obtained in Example 1 (5 parts by weight) and vitamin E (3 parts by weight) as a medicinal ingredient were thoroughly kneaded using a palette knife to obtain medicinal-ingredient-containing particles.

Example 17: Example of Manufacturing of External Preparation that Contains Medicinal-Ingredient-Containing Particles The medicinal-ingredient-containing particles obtained in Example 16 (50.0 parts by weight) were mixed with 25.0 parts by weight of mica as a clay mineral and sericite (25.0 parts by weight) as another clay mineral in a Henschel mixer. After the mixing, the mixture was pulverized once with a rotor speed mill, ZM-100, manufactured by Retsch (a 12-blade rotor was used with a 1-mm screen being attached and at a rotational speed of 14,000 rpm) to obtain body powder.

The obtained body powder provided very good slippage and an excellent feel when applied to the skin.

The present invention may be implemented in various forms without departing from its spirit and main features. Therefore, the aforementioned examples are for illustrative purposes only in every respect and should not be subjected to any restrictive interpretations. The scope of the present invention is defined only by the claims and never bound by the specification. Those modifications and variations that may lead to equivalents of claimed elements are all included within the scope of the invention.

The present application hereby claims priority on Japanese Patent Application, Tokugan, No. 2013-074210 filed Mar. 29, 2013 in Japan, the entire contents of which are hereby incorporated herein by reference.

The invention claimed is:

1. Porous resin particles which comprise a polymer of a monomer mixture which comprises:
   a mono(meth)acrylate-based monomer containing: an ethylenic unsaturated group only in a (meth)acrylic acid residue; a hydroxyl group in an alcohol residue; and at least one of an ether group and an ester group in an alcohol residue; and
   a polyfunctional vinyl-based monomer containing two or more ethylenic unsaturated groups,
   said particles having a water absorption value of from more than 400 ml to 700 ml per 100 g of said particles and an oil absorption value of from more than 400 ml to 700 ml per 100 g of said particles,
   wherein the monomer mixture contains the mono(meth)acrylate-based monomer in an amount of from 2 wt % to less than 30 wt % and the polyfunctional vinyl-based monomer in an amount of from more than 70 wt % to 98 wt %; and wherein the mono(meth)acrylate-based monomer is a compound of either general formula (1) or general formula (2):

$$CH_2=CR-COO[(C_2H_4O)_l(C_3H_6O)_m]-H \quad (1)$$

where R is either H or $CH_3$, l is 0 to 50, m is 0 to 50, and l+m>1, and $$CH_2=CR-COOCH_2CH_2O(CO(CH_2)_5O)_p-H \quad (2)$$

where R is either H or CH3, and p is 1 to 50.

2. The porous resin particles as set forth in claim 1, wherein the monomer mixture further comprises another monofunctional vinyl-based monomer having one ethylenic unsaturated group, the other monofunctional vinyl-based monomer containing at least alkyl(meth)acrylate.

3. The porous resin particles as set forth in 1, wherein the polyfunctional vinyl-based monomer is a polyfunctional (meth)acrylate-based monomer having two or more ethylenic unsaturated groups.

4. The porous resin particles as set forth in claim 1, wherein said particles have a specific surface area of from 3 $m^2/g$ to 500 $m^2/g$.

5. The porous resin particles as set forth in claim 1, wherein said particles have a pore diameter of from 4 nm to 20 nm.

6. A method of manufacturing porous resin particles having a water absorption value of from more than 400 ml to 700 ml per 100 g of said particles and an oil absorption value of from more than 400 ml to 700 ml per 100 g of said particles according to claim 1, which comprises the step of suspension-polymerizing a monomer mixture in the presence of a non-polymerizable organic solvent as a pore-forming agent, the monomer mixture comprising:
   a mono(meth)acrylate-based monomer in an amount of from 2 wt % to less than 30 wt % containing: an ethylenic unsaturated group only in a (meth)acrylic acid residue; a hydroxyl group in an alcohol residue, and at least one of an ether group and an ester group in an alcohol residue; and
   a polyfunctional vinyl-based monomer in an amount of from more than 70 wt % to 98 wt % containing two or more ethylenic unsaturated groups,
   in said step, the pore-forming agent being used in an amount of from 200 parts by weight to 500 parts by weight per 100 parts by weight of the monomer mixture, wherein the mono(meth)acrylate-based monomer is a compound of either general formula (1) or general formula (2):

$$CH_2=CR-COO[(C_2H_4O)_l(C_3H_6O)_m]-H \quad (1)$$

where R is either H or $CH_3$, l is 0 to 50, m is 0 to 50, and l+m>1, and $$CH_2=CR-COOCH_2CH_2O(CO(CH_2)_5O)_p-H \quad (2)$$

where R is either H or CH3, and p is 1 to 50.

7. The method of manufacturing porous resin particles as set forth in claim 6, wherein the pore-forming agent is an acetate ester.

8. A dispersion liquid which comprises: the porous resin particles as set forth in claim 1; and at least one dispersion medium selected from the group consisting of water and alcohols.

9. An external preparation which comprises the porous resin particles as set forth in claim 1.

10. Medicinal-ingredient-containing particles which comprise: the porous resin particles as set forth in claim 1; and a medicinal ingredient.

11. An external preparation which comprises the medicinal-ingredient-containing particles as set forth in claim 10.

12. The external preparation as set forth in claim 9, wherein said external preparation is a powdery cosmetic material.

13. A coating material which comprises the porous resin particles as set forth in claim 1.

14. A light diffusion member which comprises the porous resin particles as set forth in claim 1.

15. A liquid-chromatography separating agent which comprises the porous resin particles as set forth in claim 1.

16. The external preparation as set forth in claim 11, wherein said external preparation is a powdery cosmetic material.

* * * * *